US012589204B2

(12) United States Patent
Hayter et al.

(10) Patent No.: US 12,589,204 B2
(45) Date of Patent: Mar. 31, 2026

(54) ARTIFICIAL PANCREAS INTEGRATED CGM ARCHITECTURES AND DESIGNS

(71) Applicant: ABBOTT DIABETES CARE INC., Alameda, CA (US)

(72) Inventors: Gary Alan Hayter, Oakland, CA (US); Erwin Satrya Budiman, Fremont, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 381 days.

(21) Appl. No.: 17/473,098

(22) Filed: Sep. 13, 2021

(65) Prior Publication Data

US 2021/0402093 A1 Dec. 30, 2021

Related U.S. Application Data

(63) Continuation of application No. 16/017,584, filed on Jun. 25, 2018, now Pat. No. 11,116,898.

(Continued)

(51) Int. Cl.
*A61M 5/172* (2006.01)
*G16H 20/17* (2018.01)
(Continued)

(52) U.S. Cl.
CPC .......... *A61M 5/1723* (2013.01); *G16H 20/17* (2018.01); *G16H 40/63* (2018.01); *G16H 50/20* (2018.01);
(Continued)

(58) Field of Classification Search
CPC ............ A61M 5/1723; A61M 5/14244; A61M 2205/3303; A61M 2205/3561;
(Continued)

(56) References Cited

U.S. PATENT DOCUMENTS 2,892,990 A 6/1959 Werndl
4,392,849 A 7/1983 Petre et al.
(Continued)

FOREIGN PATENT DOCUMENTS

EP 1 391 728 2/2004
EP 1 413 245 4/2004
(Continued)

OTHER PUBLICATIONS

U.S. Appl. No. 60/606,334, filed Aug. 31, 2004, Griffith, et al.
(Continued)

*Primary Examiner* — Michael J Tsai
*Assistant Examiner* — Justin L Zamory
(74) *Attorney, Agent, or Firm* — Sterne, Kessler, Goldstein & Fox P.L.L.C.

(57) ABSTRACT

A system for managing a patient's glucose level includes a glucose sensor to generate and store data signals for measurements of the patient's glucose level made by the glucose sensor; an insulin pump; and sensor electronics operatively coupled to the glucose sensor, the sensor electronics comprising a memory storing one or more predetermined characteristics associated with the sensor electronics; and a computing device in electronic communication with the sensor electronics. The computing device comprises a processor configured to operate the sensor electronics to (i) receive the generated data signals, (ii) obtain the one or more predetermined sensor characteristics from the memory and (iii) execute a closed-loop algorithm to provide insulin delivery instructions to an insulin pump by at least using the data signals and predetermined characteristics.

18 Claims, 4 Drawing Sheets

Related U.S. Application Data

(60) Provisional application No. 62/525,164, filed on Jun. 26, 2017.

(51) Int. Cl.

| | |
|---|---|
| *G16H 40/63* | (2018.01) |
| *G16H 50/20* | (2018.01) |
| *G16H 50/70* | (2018.01) |
| *A61M 5/142* | (2006.01) |

(52) U.S. Cl.
CPC ... *G16H 50/70* (2018.01); *A61M 2005/14208* (2013.01); *A61M 5/14244* (2013.01); *A61M 2205/3303* (2013.01); *A61M 2205/3561* (2013.01); *A61M 2205/3584* (2013.01); *A61M 2205/50* (2013.01); *A61M 2205/502* (2013.01); *A61M 2205/52* (2013.01); *A61M 2230/201* (2013.01)

(58) Field of Classification Search
CPC ...... A61M 2205/3584; A61M 2205/50; A61M 2205/502; A61M 2205/52; G16H 20/17
See application file for complete search history.

(56) References Cited

U.S. PATENT DOCUMENTS

| | | | |
|---|---|---|---|
| 4,561,963 A | 12/1985 | Owen et al. | |
| 4,639,062 A | 1/1987 | Taniguchi et al. | |
| 4,650,547 A | 3/1987 | Gough | |
| 4,703,756 A | 11/1987 | Gough et al. | |
| 4,750,496 A | 6/1988 | Reinhart et al. | |
| 4,752,935 A | 6/1988 | Beck | |
| 4,861,454 A | 8/1989 | Ushizawa et al. | |
| 5,034,112 A | 7/1991 | Murase et al. | |
| 5,089,112 A | 2/1992 | Skotheim et al. | |
| 5,145,381 A | 9/1992 | Volz | |
| 5,165,407 A | 11/1992 | Wilson et al. | |
| 5,264,103 A | 11/1993 | Yoshioka et al. | |
| 5,352,351 A | 10/1994 | White et al. | |
| 5,390,671 A | 2/1995 | Lord et al. | |
| 5,391,250 A | 2/1995 | Cheney et al. | |
| 5,411,647 A | 5/1995 | Johnson et al. | |
| 5,482,473 A | 1/1996 | Lord et al. | |
| 5,497,772 A | 3/1996 | Schulman et al. | |
| 5,529,676 A | 6/1996 | Maley et al. | |
| 5,568,806 A | 10/1996 | Cheney, II et al. | |
| 5,570,300 A * | 10/1996 | Henry ................... G01F 15/024 | |
| | | | 702/45 |
| 5,591,137 A | 1/1997 | Stevens | |
| 5,593,852 A | 1/1997 | Heller et al. | |
| 5,695,623 A | 12/1997 | Michel et al. | |
| 5,700,360 A | 12/1997 | Chan et al. | |
| 5,733,259 A | 3/1998 | Valcke et al. | |
| 5,786,439 A | 7/1998 | Van Antwerp et al. | |
| 5,791,344 A | 8/1998 | Schulman et al. | |
| 5,863,400 A | 1/1999 | Drummond et al. | |
| 6,001,067 A | 12/1999 | Shults et al. | |
| 6,081,736 A | 6/2000 | Colvin et al. | |
| 6,088,608 A | 7/2000 | Schulman et al. | |
| 6,096,268 A | 8/2000 | Inbar | |
| 6,103,033 A | 8/2000 | Say et al. | |
| 6,168,957 B1 | 1/2001 | Matzinger et al. | |
| 6,175,752 B1 | 1/2001 | Say et al. | |
| 6,180,221 B1 | 1/2001 | Crotzer et al. | |
| 6,203,354 B1 | 3/2001 | Kuwahara et al. | |
| 6,212,417 B1 | 4/2001 | Ikeda et al. | |
| 6,233,471 B1 | 5/2001 | Berner et al. | |
| 6,237,394 B1 | 5/2001 | Harris et al. | |
| 6,248,067 B1 | 6/2001 | Causey, III et al. | |
| 6,275,717 B1 | 8/2001 | Gross et al. | |
| 6,340,588 B1 | 1/2002 | Nova et al. | |
| 6,360,888 B1 | 3/2002 | McIvor et al. | |
| 6,366,794 B1 | 4/2002 | Moussy et al. | |
| 6,368,141 B1 | 4/2002 | VanAntwerp et al. | |
| 6,400,974 B1 | 6/2002 | Lesho | |
| 6,424,847 B1 | 7/2002 | Mastrototaro et al. | |
| 6,475,372 B1 | 11/2002 | Ohara et al. | |
| 6,475,750 B1 | 11/2002 | Han et al. | |
| 6,522,903 B1 | 2/2003 | Berman et al. | |
| 6,558,321 B1 | 5/2003 | Burd et al. | |
| 6,558,351 B1 | 5/2003 | Steil et al. | |
| 6,560,471 B1 | 5/2003 | Heller et al. | |
| 6,565,509 B1 | 5/2003 | Say et al. | |
| 6,587,704 B1 | 7/2003 | Fine et al. | |
| 6,741,877 B1 | 5/2004 | Shults et al. | |
| 6,809,653 B1 | 10/2004 | Mann et al. | |
| 6,835,553 B2 | 12/2004 | Han et al. | |
| 6,850,859 B1 | 2/2005 | Schuh | |
| 6,923,763 B1 | 8/2005 | Kovatchev et al. | |
| 6,931,327 B2 | 8/2005 | Goode, Jr. et al. | |
| 6,965,791 B1 | 11/2005 | Hitchcock et al. | |
| 6,990,366 B2 | 1/2006 | Say et al. | |
| 7,220,387 B2 | 5/2007 | Flaherty et al. | |
| 7,299,082 B2 | 11/2007 | Feldman et al. | |
| 7,404,796 B2 | 7/2008 | Ginsberg | |
| 7,491,303 B2 | 2/2009 | Sakata et al. | |
| 7,525,315 B2 | 4/2009 | Fredette et al. | |
| 8,282,549 B2 | 10/2012 | Brauker et al. | |
| 8,396,670 B2 | 3/2013 | St-Pierre | |
| 9,241,631 B2 | 1/2016 | Valdes et al. | |
| 9,504,471 B2 | 11/2016 | Vaitekunas et al. | |
| 9,808,574 B2 | 11/2017 | Yodfat et al. | |
| 10,709,364 B2 | 7/2020 | Kamath et al. | |
| 10,820,842 B2 | 11/2020 | Harper | |
| 10,827,954 B2 | 11/2020 | Hoss et al. | |
| 10,874,338 B2 | 12/2020 | Stafford | |
| 10,881,341 B1 | 1/2021 | Curry et al. | |
| 10,945,647 B2 | 3/2021 | Mazza et al. | |
| 10,945,649 B2 | 3/2021 | Lee et al. | |
| 10,952,653 B2 | 3/2021 | Harper | |
| 10,959,654 B2 | 3/2021 | Curry et al. | |
| 10,966,644 B2 | 4/2021 | Stafford | |
| 10,973,443 B2 | 4/2021 | Funderburk et al. | |
| 11,000,213 B2 | 5/2021 | Kamath et al. | |
| 11,000,216 B2 | 5/2021 | Curry et al. | |
| 11,013,440 B2 | 5/2021 | Lee et al. | |
| 11,020,031 B1 | 6/2021 | Simpson et al. | |
| 11,064,917 B2 | 7/2021 | Simpson et al. | |
| 11,116,898 B2 * | 9/2021 | Hayter ................ A61M 5/1723 | |
| 11,141,084 B2 | 10/2021 | Funderburk et al. | |
| 2002/0010390 A1 | 1/2002 | Guice et al. | |
| 2002/0032531 A1 | 3/2002 | Mansky et al. | |
| 2002/0043651 A1 | 4/2002 | Darrow et al. | |
| 2002/0057993 A1 | 5/2002 | Maisey et al. | |
| 2002/0161288 A1 | 10/2002 | Shin et al. | |
| 2002/0177764 A1 | 11/2002 | Sohrab | |
| 2003/0003524 A1 | 1/2003 | Taniike et al. | |
| 2003/0060753 A1 | 3/2003 | Starkweather et al. | |
| 2003/0065536 A1 | 4/2003 | Hansen et al. | |
| 2003/0076082 A1 | 4/2003 | Morgan et al. | |
| 2003/0100040 A1 | 5/2003 | Bonnecaze et al. | |
| 2003/0130616 A1 | 7/2003 | Steil et al. | |
| 2003/0144581 A1 | 7/2003 | Conn et al. | |
| 2003/0153900 A1 | 8/2003 | Aceti et al. | |
| 2003/0187338 A1 | 10/2003 | Say et al. | |
| 2003/0212317 A1 | 11/2003 | Kovatchev et al. | |
| 2004/0018486 A1 | 1/2004 | Dunn et al. | |
| 2004/0022438 A1 | 2/2004 | Hibbard | |
| 2004/0106858 A1 | 6/2004 | Say et al. | |
| 2004/0106860 A1 | 6/2004 | Say et al. | |
| 2004/0122353 A1 * | 6/2004 | Shahmirian ......... A61M 5/1723 | |
| | | | 700/282 |
| 2004/0127777 A1 | 7/2004 | Ruchti et al. | |
| 2004/0133164 A1 | 7/2004 | Funderburk et al. | |
| 2004/0147872 A1 | 7/2004 | Thompson | |
| 2004/0244151 A1 | 12/2004 | Sakata et al. | |
| 2005/0004439 A1 | 1/2005 | Shin et al. | |
| 2005/0027180 A1 | 2/2005 | Goode, Jr. et al. | |
| 2005/0027463 A1 | 2/2005 | Goode, Jr. et al. | |
| 2005/0038332 A1 | 2/2005 | Saidara et al. | |
| 2005/0043598 A1 | 2/2005 | Goode, Jr. et al. | |
| 2005/0059871 A1 | 3/2005 | Gough et al. | |
| 2005/0069892 A1 | 3/2005 | Iyengar et al. | |

(56)         References Cited

U.S. PATENT DOCUMENTS

| | | | |
|---|---|---|---|
| 2005/0143636 | A1 | 6/2005 | Zhang et al. |
| 2005/0151976 | A1 | 7/2005 | Toma |
| 2005/0176136 | A1 | 8/2005 | Burd et al. |
| 2005/0192557 | A1 | 9/2005 | Brauker et al. |
| 2005/0215871 | A1 | 9/2005 | Feldman et al. |
| 2005/0239154 | A1 | 10/2005 | Feldman et al. |
| 2005/0242479 | A1 | 11/2005 | Petisce et al. |
| 2005/0245799 | A1 | 11/2005 | Brauker et al. |
| 2006/0011474 | A1 | 1/2006 | Schulein et al. |
| 2006/0016700 | A1 | 1/2006 | Brister et al. |
| 2006/0019327 | A1 | 1/2006 | Brister et al. |
| 2006/0020187 | A1 | 1/2006 | Brister et al. |
| 2006/0020188 | A1 | 1/2006 | Kamath et al. |
| 2006/0020192 | A1 | 1/2006 | Brister et al. |
| 2006/0025663 | A1 | 2/2006 | Talbot et al. |
| 2006/0036143 | A1 | 2/2006 | Brister et al. |
| 2006/0094944 | A1 | 5/2006 | Chuang |
| 2006/0094945 | A1 | 5/2006 | Barman et al. |
| 2006/0142651 | A1 | 6/2006 | Brister et al. |
| 2006/0173406 | A1 | 8/2006 | Hayes et al. |
| 2006/0189863 | A1 | 8/2006 | Peyser et al. |
| 2006/0258929 | A1 | 11/2006 | Goode, Jr. et al. |
| 2006/0258959 | A1 | 11/2006 | Sode |
| 2006/0276771 | A1 | 12/2006 | Galley et al. |
| 2006/0281985 | A1 | 12/2006 | Ward et al. |
| 2006/0293576 | A1 | 12/2006 | Van Antwerp et al. |
| 2007/0073129 | A1 | 3/2007 | Shah et al. |
| 2007/0208244 | A1 | 9/2007 | Brauker et al. |
| 2007/0249922 | A1 | 10/2007 | Peyser et al. |
| 2007/0299617 | A1 | 12/2007 | Willis |
| 2008/0021436 | A1 | 1/2008 | Wolpert et al. |
| 2008/0119710 | A1 | 5/2008 | Reggiardo et al. |
| 2008/0172205 | A1 | 7/2008 | Breton et al. |
| 2008/0270162 | A1* | 10/2008 | Machacek .......... G05B 23/0221 |
| | | | 702/182 |
| 2008/0300572 | A1 | 12/2008 | Rankers et al. |
| 2008/0312842 | A1 | 12/2008 | Hayter et al. |
| 2009/0005665 | A1 | 1/2009 | Hayter et al. |
| 2009/0012376 | A1 | 1/2009 | Agus |
| 2009/0076360 | A1 | 3/2009 | Brister et al. |
| 2009/0102678 | A1 | 4/2009 | Mazza et al. |
| 2009/0105636 | A1 | 4/2009 | Hayter et al. |
| 2009/0143659 | A1 | 6/2009 | Li et al. |
| 2009/0163789 | A1 | 6/2009 | Say et al. |
| 2009/0178459 | A1 | 7/2009 | Li et al. |
| 2009/0192380 | A1 | 7/2009 | Shariati et al. |
| 2009/0198118 | A1* | 8/2009 | Hayter ................. A61B 5/1495 |
| | | | 600/347 |
| 2009/0240120 | A1 | 9/2009 | Mensinger et al. |
| 2009/0247857 | A1 | 10/2009 | Harper et al. |
| 2009/0312622 | A1 | 12/2009 | Regittnig |
| 2010/0057040 | A1 | 3/2010 | Hayter |
| 2010/0057041 | A1 | 3/2010 | Hayter |
| 2010/0057042 | A1 | 3/2010 | Hayter |
| 2010/0057057 | A1 | 3/2010 | Hayter et al. |
| 2010/0145377 | A1 | 6/2010 | Lai et al. |
| 2010/0191472 | A1 | 7/2010 | Doniger et al. |
| 2010/0230285 | A1 | 9/2010 | Hoss et al. |
| 2010/0274515 | A1 | 10/2010 | Hoss et al. |
| 2011/0004085 | A1* | 1/2011 | Mensinger ........... A61B 5/7275 |
| | | | 600/365 |
| 2011/0077494 | A1 | 3/2011 | Doniger et al. |
| 2011/0178717 | A1 | 7/2011 | Goodnow et al. |
| 2012/0318670 | A1 | 12/2012 | Karinka et al. |
| 2013/0331667 | A1* | 12/2013 | Colvin, Jr. ......... A61B 5/14556 |
| | | | 600/316 |
| 2014/0221966 | A1* | 8/2014 | Buckingham ..... A61M 5/14244 |
| | | | 604/504 |
| 2015/0005601 | A1 | 1/2015 | Hoss et al. |
| 2016/0302701 | A1* | 10/2016 | Bhavaraju .......... A61B 5/14532 |
| 2017/0112531 | A1 | 4/2017 | Schoonmaker et al. |
| 2019/0274598 | A1 | 9/2019 | Scott et al. |

FOREIGN PATENT DOCUMENTS

| | | |
|---|---|---|
| EP | 1 413 879 | 1/2012 |
| EP | 1 07 5209 | 10/2014 |
| EP | 3 575 796 | 12/2019 |
| EP | 3 797 682 | 3/2021 |
| EP | 3 831 282 B1 | 6/2021 |
| WO | WO 98/16975 A1 | 4/1998 |
| WO | WO 99/58190 A1 | 11/1999 |
| WO | WO 00/49941 | 8/2000 |
| WO | WO 01/52727 | 7/2001 |
| WO | WO 02/058537 | 8/2002 |
| WO | WO 2002/058537 | 8/2002 |
| WO | WO 03/012422 | 2/2003 |
| WO | WO 03/032411 | 4/2003 |
| WO | WO 03/094714 | 11/2003 |
| WO | WO 2005/011489 | 2/2005 |
| WO | WO 2005/026689 | 3/2005 |
| WO | WO 2005/041766 | 5/2005 |
| WO | WO 2005/065542 | 7/2005 |
| WO | WO 2005/070287 | 8/2005 |
| WO | WO 2006/026741 | 3/2006 |
| WO | WO 2006/099151 | 9/2006 |
| WO | WO 2008/021913 | 2/2008 |
| WO | WO 2008/151452 | 12/2008 |
| WO | WO 2009/049252 | 4/2009 |
| WO | WO 2010/099507 | 9/2010 |
| WO | WO 2011/011643 | 1/2011 |
| WO | WO 2012/142502 | 10/2012 |
| WO | WO 2014/105631 A2 | 7/2014 |

OTHER PUBLICATIONS

U.S. Appl. No. 60/614,764, filed Sep. 30, 2004, Kamath, et al.
U.S. Appl. No. 61/227,967, filed Jul. 23, 2009, Hoss, et al.
Abbott's Continuous Blood Glucose Monitor Approval Soon, 3 pages (2006).
Abel, et al., "Biosensors for in vivo glucose measurement: can we cross the experimental stage", Biosensors and Bioelectronics, 17:1059-1070 (2002).
Alcock, et al., "Continuous Analyte Monitoring to Aid Clinical Practice", IEEE Engineering in Medicine and Biology, pp. 319-325 (1994).
Bard, et al., Electrochemical Methods, Fundamentals and Applications, pp. 174-175 (1980).
Black, J., et al., Handbook of Biomaterial Properties, Springer-Science+Business Media, B.V., 61 pages (1998).
Cengiz, et al., "A Tale of Two Compartments: Interstitial Versus Blood Glucose Monitoring", Diabetes Technology & Therapeutics, 11(1):S-11-S16 (2009).
Chen, et al., "Glucose microbiosensor based on alumina sol gel matrix/eletropolymerized composite membrane", Biosensors and Bioelectronics, 17:1005-1013 (2002).
Chen, et al., "In Situ Assembled Mass-Transport Controlling Micromembranes and Their Application in Implanted Amperometric Glucose Sensors", Analytical Chemistry, 72(16):3757-3763 (2000).
Chen, et al., "In vivo Glucose Monitoring with Miniature "Wired" Glucose Oxidase Electrodes", Analytical Sciences 2001, 17:i297-i300 (2001).
Chen, et al., "Defining the Period of Recovery of the Glucose Concentration after its Local Perturbation by the Implantation of a Miniature Sensor", Clin Chem Lab Med 2002; 40 (8): 786-789.
Children with Diabetes—Report from Diabetes Technology Meeting, 3 pages (2003).
Chung, "In vitro Evaluation of the Continuous Monitoring Glucose Sensors with Perfluorinated Tetrafluoroethylene Coatings", Bull. Korean Chem. Soc., 24(4):514-516 (2003).
Claremont, D.J., et al., In vivo chemical sensors and biosensors in clinical medicine, pp. 356-376.
Csoregi E. et al., "Design, Chracterization, And One-Point In Vivo Calibration of a Subcutaniously Implanted Glucose Electrode",, Anal. Chem 1994, 66: 3131-3138.
De Block, et al., "Minimally-Invasive and Non-Invasive Continuous Glucose Monitoring Systems: Indications, Advantages, Limitations and Clinical Aspects", Current Diabetes Reviews, 4:159-168 (2008).

(56)  References Cited

OTHER PUBLICATIONS

Declaration of John Mastrototaro, Ph.D. (2022).

Determination of Regulatory Review Period for Purposes of Patent Extension; SEVENFACT, Department of Health and Human Services, Food and Drug Administration, Notice, Federal Register, 86(211):60827-60829 (2021).

Diabetes Close Up, Conferences #2, Diabetes Technology—DAWN Summit, pp. 1-8, (2003).

Dufresne, A.T., et al., How reliable are trial dates relied on by the PTAB in the Fintiv analysis?, Perkins Coie, 1600 PTAB & Beyond, 4 pages (2022).

Federal Register, vol. 86, No. 211, pp. 60827-60829 (2021).

Feldman, et al., "A Continuous Glucose Sensor Based on Wired Enzyme™ Technology—Results from a 3-Day Trial in Patients with Type 1 Diabetes", Diabetes Technology & Therapeutics, 5(5):769-779 (2003).

Fraser, "An Introduction to in vivo Biosensing: Progress and Problems", Biosensors in the Body: Continuous in vivo Monitoring, pp. 1-56 (1997).

FreeStyle Navigator Continuous Glucose Monitoring System, Summary of Safety and Effectiveness Data in support of Pre-Market Approval (PMA) No. P050020, Abbott Diabetes Care, 27 pages (2008).

FreeStyle Navigator Continuous Glucose Monitoring System, User Guide, Abbott Diabetes Care Inc., 195 pages (2008).

FreeStyle Navigator Continuous Glucose Monitoring System, User's Guide, Abbott Diabetes Care Inc., 38 pages, (DATE).

Frost, et al., "Implantable chemical sensors for real-time clinical monitoring: progress and challenges", Current Opinion in Chemical Biology, 6:633-641 (2002).

Fujipoly, New High Performance Silver ZEBRA® Connector, Fujipoly Data Sheet No. FPDS 01-34/Version 2, 7 pages (2002).

Fujipoly, New High Performance Silver ZEBRA® Connector, Fujipoly Data Sheet No. FPDS 01-34/Version 5, 7 pages (2006).

Fujipoly, New High Performance Silver ZEBRA® Connector, Fujipoly Data Sheet No. FPDS 01-34/Version 5, 7 pages (2007).

Fujipoly, ZEBRA® Elastomeric Connectors, Fujipoly America Corp—Zebra—Zebra Carbon, 3 pages (2003).

Gandrud, "Functionality of the MiniMed Continuous Glucose Monitoring System", Abstracts of the 64th Scientific Sessions of the American Diabetes Association, vol. 50, Supplement 2, Jun. 4-8, 2004.

Gerritsen, et al., "Performance of subcutaneously implanted glucose sensors for continuous monitoring", The Netherlands Journal of Medicine, 54:167-179 (1999).

Gerritsen, et al., "Subcutaneously implantable glucose sensors in patients with diabetes mellitus; still many problems", Dutch Journal of Medicine, 146(28):1313-1316 (2002) (with English Machine Translation).

Guardian® REAL-Time, Continuous Glucose Monitoring System, User Guide, Medtronic MiniMed, Inc., 181 pages (2006).

Guardian® RT, Continuous Glucose Monitoring System, REF MMT-7900, User Guide, Medtronic MiniMed, 128 pages (2005).

Heide, C., Silicone Rubber for Medical Device Applications, Medical Plastics and Biomaterials, Special Section, Medical Device & Diagnostic Industry, 7 pages (1999).

Heinemann, "Continuous Glucose Monitoring by Means of the Microdialysis Technique: Underlying Fundamental Aspects", Diabetes Technology & Therapeutics, 5(4):545-561 (2003).

Heinemann, Lutz, et al., Benefits and Limitations of MARD as a Performance Parameter for Continuous Glucose Monitoring in the Interstitial Space, Journal of Diabetes Science and Technology 2020, vol. 14 (1) 135-150.

Heise, et al., "Hypoglycemia Warning Signal and Glucose Sensors: Requirements and Concepts", Diabetes Technology & Therapeutics, 5(4):563-571 (2003).

Heller, "Implanted Electrochemical Glucose Sensors for the Management of Diabetes", Annu. Rev. Biomed. Eng., 01:153-175 (1999).

Heller, A et al., Electrochemical Glucose Sensors and Their Applications in Diabetes Management, Chemical Reviews, vol. 108, No. 7, pp. 2482-2505 (2008).

Heller, A., Integrated Medical Feedback Systems for Drug Delivery, AIChE Journal, vol. 51, No. 4, pp. 1054-1066 (2005).

Heller, et al., "Electrochemistry in Diabetes Management", Accounts of Chemical Research, 43(7):963-973 (2010).

"In Vivo Glucose Sensing", Chemical Analysis, A Series of Monographs on Analytical Chemistry and its Applications, vol. 174, 466 pages (2010).

Jiménez, et al., "Glucose sensor based on an amperometric microelectrode with a photopolymerizable enzyme membrane", Sensors and Actuators B, 26-27:421-424 (1995).

Johnson K.W., et al. "Reduction of Electrooxidizable Interferents Effects: Optimizaton of the Applied Potential For Amperometric Glucose Sensors", Elctroanalysis 6(1994) 321-326.

Johnson, et al., "In Vivo evaluation of an electroenzymatic glucose sensor implanted in subcutaneous tissue", Biosensors & Bioelectronics, 7:709-714 (1992).

Kass, D., Fintiv Fails: PTAB Uses 'Remarkably Inaccurate' Trial Dates, Law 360, Portfolio Media, Inc., 1 page (2021).

Koudelka, et al., "In-vivo Behaviour of Hypodermically Implanted Microfabricated Glucose Sensors", Biosensors & Bioelectronics, 6:31-36 (1991).

Koudelka-Hep, "Electrochemical Sensors for in vivo Glucose Sensing", Biosensors in the Body: Continuous in vivo Monitoring, pp. 57-77 (1997).

Kovatchev, B., et al., Evaluating the Accuracy of Continuous Glucose-Monitoring Sensors, Diabetes Care, vol. 27, No. 8, pp. 1922-1928 (2004).

Kreith, et al., The CRC Handbook of Mechanical Engineering, (1998).

Krieth, Frank, et al., The CRC Handbook of Mechanical Engineer, Second Edition, CRC Press Inc. (2004).

Kvist, et al., "Recent Advances in Continuous Glucose Monitoring: Biocompatibility of Glucose Sensors for Implantation in Subcutis", Journal of Diabetes Science and Technology, 1(5):746-752 (2007).

"Leading the Way for You and Your Patients with Continuous Glucose Monitoring" Brochure, Dexcom Inc., 12 pages (2010).

Lodwig, et al., "Continuous Glucose Monitoring with Glucose Sensors: Calibration and Assessment Criteria", Diabetes Technology & Therapeutics, 5(4):573-587 (2003).

Ming Li, et al., "Implantable Electrochemical Sensors for Biomedical and Clinical Applications: Progress, Problems, and Future Possibilities", Current Medicinal Chemistry, 14:937-951 (2007).

Moatti-Sirat, et al., "Evaluating in vitro and in vivo the interference of ascorbate and acetaminophen on glucose detection by a needle-type glucose sensor", Biosensors and Bioelectronics, 7(5):345-352 (1992).

Moussy, F., et al., 32.2: Implantable Glucose Sensor: Progress and Problems, IEEE, pp. 270-273 (2002).

Moussy, F., et al., Performance of Subcutaneously Implanted Needle-Type Glucose Sensors Employing a Novel Trilayer Coating, Analytical Chemistry, vol. 65, No. 15, pp. 2072-2077 (1993).

Nishida, et al., "Development of a ferrocene-mediated needle-type glucose sensor covered with newly designed biocompatible membrane, 2-methacryloyloxyethyl phosphorylcholine-co-n-butyl methacrylate", Medical Progress through Technology, 21:91-103 (1995).

Onuki, et al., "A Review of the Biocompatibility of Implantable Devices: Current Challenges to Overcome Foreign Body Response", Journal of Diabetes Science and Technology, 2(6):1003-1015 (2008).

Original Premarket Approval Application, FreeStyle Navigator Continuous Glucose Monitoring System, Section VII: Manufacturing Section Steven Label Sensor Sheet Validation Plan, vol. 28 of 31, TheraSense, Inc., 61 pages (2005).

Poitout, et al., "Calibration in dogs of a subcutaneous miniaturized glucose sensor using a glucose meter for blood glucose determination", Biosensors & Bioelectronics, 7:587-592 (1992).

Premarket Approval Application Amendment, FreeStyle Navigator Continuous Glucose Monitoring System, vol. 2 of 39, Section III, Device Description, Abbott Diabetes Care, Inc., 89 pages (2006).

(56)                    References Cited

OTHER PUBLICATIONS

Princy, et al., "Studies on Conductive Silicone Rubber Compounds", Journal of Applied Polymer Science, 69:1043-1050 (1998).
Rebrin, et al., "Subcutaneous glucose predicts plasma glucose independent of insulin: implications for continuous monitoring", American Journal of Physiology-Endocrinology and Metabolism, 277(3):E561-E571 (1999).
Reiterer, Florian, et al., Significance and Reliability of MARD for the Accuracy of CGM Systems, Journal of Diabetes Science and Technology 2017, vol. 11 (1) 59-67.
Renard, "Implantable glucose sensors for diabetes monitoring", Min Invas Ther & Allied Technol, 13(2):78-86 (2004).
Rhodes, et al., "Prediction of Pocket-Portable and Implantable Glucose Enzyme Electrode Performance from Combined Species Permeability and Digital Simulation Analysis", Analytical Chemistry, 66(9):1520-1529 (1994).
Robert, "Continuous Monitoring of Blood Glucose", Horm Res 57(suppl 1):81-84 (2002).
Schlosser, et al., "Biocompatibility of Active Implantable Devices", Biosensors in the Body: Continuous in vivo Monitoring, pp. 139-170 (1997).
Schmidt, et al., "Calibration of a wearable glucose sensor", The International Journal of Artificial Organs, 15(1):55-61 (1992).
Schmidtke, et al., "Accuracy of the One-Point in Vivo Calibration of "Wired" Glucose Oxidase Electrodes Implanted in Jugular Veins of Rats in Periods of Rapid Rise and Decline of the Glucose Concentration", Anal. Chem., 70:2149-2155 (1998).
Seal Design Guide, Apple Rubber Products Inc., 190 pages (1999).
Seal Design Guide, Apple Rubber Products Inc., 122 pages (2020).
Silastic® MDX4-4210, BioMedical Grade Elastomer, Dow Corning, Ref. No. 51-0202K-01, pp. 1-4 (2005).
Silicone Rubber for Medical Device Applications, Medical Device and Diagnostic Industry Qmed, Nov. 1, 1999 Column.
Standard Test Method for Rubber Property-Durometer Hardness, ASTM International, Designation: D 2240-05, 13 pages (2005).
The CGM Resource Center References/Bibliography, 14 pages, LBL 010629 Rev 02.
TheraSense Files Premarket Approval Application for Freestyle Navigator(TM) Cont, 3 pages (2003).
Therasense Navigates Continuous Glucose Monitor PMA, Prepares for Flash, The Gray Sheet, vol. 29, No. 37, 2 pages (2003).
Tierney, et al., "Effect of Acetaminophen on the Accuracy of Glucose Measurements Obtained with the GlucoWatch Biographer", Diabetes Technology & Therapeutics, 2(2):199-207 (2000).
U.S. Food & Drug Administration, Premarket Approval (PMA) for Freestyle Navigator Continuous Glucose Monitor, 6 pages, Notice Date: Apr. 1, 2008.
United States Securities and Exchange Commission, Form 10-K, 59 pages (2005).
United States Securities and Exchange Commission, Form S-1, 309 pages (2005).
Velho, et al., "Strategies for Calibrating a Subcutaneous Glucose Sensor", Biomed. Biochim. Acta, vol. 48, pp. 957-964 (1989).
Voskerician, et al., "Sensor Biocompatibility and Biofouling in Real-Time Monitoring", Wiley Encyclopedia of Biomedical Engineering, (John Wiley & Sons, Inc.), pp. 1-19 (2006).
Ward, "A Review of the Foreign-body Response to Subcutaneously-implanted Devices: The Role of Macrophages and Cytokines in Biofouling and Fibrosis", Journal of Diabetes Science and Technology, 2(5):768-777 (2008).
Ward, et al., "A new amperometric glucose microsensor: in vitro and short-term in vivo evaluation", Biosensors & Bioelectronics, 17:181-189 (2002).
Ward, W.K., et al., A Wire-Based Dual-Analyte Sensor for Glucose and Lactane: In Vitro and in Vivo Evaluation, Military Metabolic Monitoring, edited by Friedl, C.K.E., Diabetes Technology & Therapeutics, vol. 6, No. 3, pp. 389-401 (2004).
Ward, W.K., et al., Rise in background current over time in a subcutaneous glucose sensor in the rabbit: relevance to calibration and accuracy, Biosensors & Bioelectronics, 15, pp. 53-61 (2000).

Wilson, G.S., et al., Chapter 1, Introduction to the Glucose Sensing Problem, In Vivo Glucose Sensing, edited by D.D. Cunningham et al., pp. 1-27 (2010).
Yang, et al., "Glucose Biosensors Based on Oxygen Electrode with Sandwich-Type Membranes", Annals of Biomedical Engineering, 23:833-839 (1995).
Yang, et al., "Glucose Biosensors with Enzyme Entrapped in Polymer Coating", Biomedical Instrumentation & Technology, 29(2):125-133 (1995).
Z-Carbon LCD Connector, 2 pages (2004).
Z-Silver Connector, 2 pages (2004).
U.S. Appl. No. 16/017,584 (U.S. Pat. No. 11,116,898), filed Jun. 25, 2018 (Sep. 14, 2021).
U.S. Appl. No. 16/017,584, Aug. 16, 2021 Issue Fee Payment.
U.S. Appl. No. 16/017,584, May 17, 2021 Notice of Allowance.
U.S. Appl. No. 16/017,584, May 5, 2021 Amendment and Request for Continued Examination (RCE).
U.S. Appl. No. 16/017,584, Apr. 13, 2021 Advisory Action.
U.S. Appl. No. 16/017,584, Mar. 5, 2021 Response after Final Action.
U.S. Appl. No. 16/017,584, Jan. 6, 2021 Final Office Action.
U.S. Appl. No. 16/017,584, Dec. 18, 2020 Response to Non-Final Office Action.
U.S. Appl. No. 16/017,584, Jun. 25, 2020 Non-Final Office Action.
"DexCom's 7-Day STS Continuous Glucose Monitoring System", Jun. 1, 2007 https://newatlas.com/dexcoms-7-day-sts-continuous-glucose-monitoring-system/7376/.
"Within Definition & Meaning" retrieved from "https://www.dictionary.com/browse/within" on Sep. 9, 2022, 5 pages.
Chen, et al., "A novel fault-tolerant sensor system for sensor drift compensation", Sensors and Actuators, A 147:623-632 (2008).
FreeStyle Navigator Continuous Glucose Monitoring System, User's Guide, Abbott Diabetes Care Inc., 38 pages, (2008).
Kalivas, et al., "Compensation for Drift and Interferences in Multicomponent Analysis", Laboratory for Chemometrics, Department of Chemistry, University of Washington, 38 pages (1982).
Thévenot, et al., "Electrochemical Biosensors: Recommended Definitions and Classification (Technical Report)", Pure Appl. Chem. 71(12):2333-2348 (1999).
U.S. Appl. No. 12/842,013 Office Action mailed Aug. 26, 2015.
U.S. Appl. No. 12/842,013 Office Action mailed Mar. 23, 2016.
U.S. Appl. No. 12/842,013 Office Action mailed Nov. 6, 2014.
Walt, et al., "The chemistry of enzyme and protein immobilization with glutaraldehyde", Trends in Analytical Chemistry, 13(10):425-430 (1994).
Zhang, "Investigations of potentially implantable glucose sensors", University of Kansas, 24 pages (1991).
U.S. Appl. No. 60/614,683, filed Sep. 30, 2004, Brister et al.
Aleppo et al. "REPLACE-BG: A Randomized Trial Comparing Continuous Glucose Monitoring with and Without Routine Blood Glucose Monitoring in Adults with Well-Controlled Type 1 Diabetes" Diabetes Care, 2017, 40:538-545.
Amiel et al., "Training in flexible, intensive insulin management to enable dietary freedom in people with type 1 diabetes: dose adjustment for normal eating (DAFNE) randomized controlled trial" BMJ, 2002, 325; 6 pages.
Amiel et al., "Hypoglycaemia in Type 2 diabetes", Diabetic Medicine, 2008, 25:245-254.
"Animas® VibeTM, the First Integrated Offering from Animas Corporation and Dexcom, Inc, Receives European CE Mark Approval", Products & Operating Company, 2011, 4 pages.
Bailey et al., "Reduction in Hemoglobin A1c with Real-Time Continuous Glucose Monitoring: Results from a 12-Week Observational Study" Diabetes Technology & Therapeutics, 2007, 9(3):203-210.
CGMS® iProTM Continuous Glucose Recorder, User Guide, Medtronic MiniMed, 2007, 36 pages.
Choudhary et al., "Hypoglycaemia in the treatment of diabetes mellitus" Oxford Textbook of Endocrinology and Diabetes, 2011, pp. 1849-1860.
COHRlastic Silicone Rubber Products, Saint-Gobain Performance Plastics, 7 pages (2002).

(56)             References Cited

OTHER PUBLICATIONS

"Continuous Glucose Sensors: Continuing Questions about Clinical Accuracy" Journal of Diabetes Science and Technology, 2007; 1(5):669-675.

Cryer, "Preventing Hypoglycaemia: what is the appropriate glucose alert value?" Diabetologia, 2009, 53:35-37.

Cunningham et al., "In Vivo Glucose Sensing", Wiley, 2010, pp. 143-147.

"Defining and Reporting Hypoglycemia in Diabetes", American Diabetes Association, Diabetes Care, 2005, 28(5):1245-1249.

DeVries, "Glucose Sensing Issues For the Artificial Pancreas" Journal of Diabetes Science and Technology, 2008, 2(4):732-734.

Dexcom G4 Continuous Glucose Monitoring System, User's Guide, Dexcom, 2013, 156 pages.

"Diabetes (type 1), PSP Top 10", James, Lind Alliance, Priority Setting Partnerships, 2011, 3 pages.

Elastosil® RT 602, RTV-2 Silicone Encapsulant, Version 3.00, Wacker Silicones, 2 pages (2004).

Elastosil® RTV-1 Silicone Rubber, Wacker Silicone, 16 pages (2001).

Exhibit 3, GE Silicones—Master Grade, General Electric Company, 2 pages (2003).

Exhibit 4, Elastosil® LR 3162 A, B, Version 3.00, Wacker Silicones, 3 pages (2004).

FreeStyle Navigator II Continuous Glucose Monitoring System, User's Manual, Abbott, 2015, 21 pages.

FreeStyle Navigator Continuous Glucose Monitoring System, User Guide, Abbott, 2010, 135 pages.

FreeStyle Libre 2 Flash Glucose Monitoring System, User's Manual, Abbott, 2021, 141 pages.

FreeStyle Libre 3 Continuous Glucose Monitoring System APP, User's Manual English, Abbott, 2022, 59 pages.

Frier, "Defining hypoglycaemia: what level has clinical relevance? ", Diabetologia, 2009, 52:31-34.

Garg, et al., "Improvement in Glycemic Excursions with a Transcutaneous, Real-Time Continuous Glucose Sensor", Diabetes Care, 2006, 29(12):44-50.

Garg, et al, Relationship of Fasting and Hourly Blood Glucose Levels to HbA1c Values, Diabetes Care, 2006, 6(12):2644-2649.

Glucowatch G2, Automatic Glucose Biographer and Autosensors, 2002, 70 pages.

"Guideline on clinical investigation of medicinal products in the treatment or prevention of diabetes mellitus" European Medicines Agency, May 14, 2012, 28 pages.

Heller, "Glucose Concentrations of Less Than 3.0 mmol/L (54mg/dL) Should Be Reported in Clinical Trials: A Joint Position Statement of the American Diabetes Association and the European Association for the Study of Diabetes" Diabetes Care, 2017; 40:155-157.

Innovation Milestones, 2022, 37 pages.

Internet Archive, WayBack Machine, "http://www.minimed.com/doctors/md_products_cgms_ov_completepic.shtml"; Medtronic MiniMed, 2004, 20 pages.

Mark up specification of publication No. US2007208244A1, 2007, 170 pages.

Mark up specification of publication No. WO2008130898A1, 2008, 30 pages.

National Service Framework for Diabetes: Standards, Dept. of Health, 2002, 48 pages.

Note for Guidance on Clinical Investigation of Medicinal Products in the Treatment of Diabetes Mellitus, The European Agency for the Evaluation of Medicinal Products, 2002, 12 pages.

Oliver et al., "Glucose sensors: a review of current and emerging technology", Diabetic Medicine, 2009, 26:197-210.

Pickup et al., "Glycaemic control in type 1 diabetes during real time continuous glucose monitoring compared with self monitoring of blood glucose: meta-analysis of randomised controlled trials using individual patient data" BMJ, 2011; 14 pages.

Pickup, "Glucose monitoring", Oxford Textbook of Endocrinology and Diabetes, 2011, pp. 1861-1869.

Puhr et al., "Real-World Hypoglycemia Avoidance with a Predictive Low Glucose Alert Does Not Depend on Frequent Screen Views", Journal of Diabetes Sciences and Technology, 2004, 14(1): 83-86.

Rilestone et al., "The impact of CGM with a predictive hypoglycaemia alert function on hypoglycaemia in physical activity for people with type 1 diabetes: PACE study", Dexcom, 2022, 2 pages.

SILASTIC® 94-595, Product Information Liquid Silicone Rubber, Dow Corning, 4 pages (2002).

Sparacino et al., "Glucose Concentration can be Predicted Ahead in Time from Continuous Glucose Monitoring Sensor Time-Series", IEEE Transactions on Biomedical Engineering, 2007, 54(5):931-937.

"Standards of Medical Care in Diabetes—2009" Position Statement, American Diabetes Association, 2009, Diabetes Care, 32(1):S13-S61.

Swinnen, S.G.H.A. et al., "Changing the glucose cut-off values that define Hypoglycaemia has a major effect on reported frequencies of hypoglycaemia", Diabetologia, 2009, 52:38-41.

"The Effect of Intensive Treatment of Diabetes on the Development and Progression of Long-Term Complications in Insulin-Dependent Diabetes Mellitus" The New Journal of Medicine, 1993, 329(14):977-986.

"Type 1 diabetes: diagnosis and management of type 1 diabetes in children, young people and adults" National Institute for Clinical Excellence, Clinical Guideline 15, Jul. 2004, 113 pages.

Type 1 Diabetes Research Roadmap, "Identifying the strengths and weaknesses, gaps and opportunities of UK type 1 diabetes research; clearing a path to cure", Type 1 diabetes research roadmap, JDRF, 2013, 21 pages.

Welcome to Your FreeStyle Libre System In-Service Guide, FreeStyle Libre, Flash Glucose Monitoring System, Abbott, 2017, 22 pages.

U.S. Appl. No. 60/687,199, filed Jun. 2, 2005, Ward, et al.

U.S. Appl. No. 61/155,889, filed Feb. 26, 2009, Hoss, et al.

Atanasov, et al., "Implantation of a refillable glucose monitoring-telemetry device", Biosensors & Bioelectronics, 12(7):669-680 (1997).

Bindra, "Development of potentially implantable glucose sensors", The University of Arizona, 227 pages (1990).

Choleau, et al., "Calibration of a subcutaneous amperometric glucose sensor implanted for 7 days in diabetic patients Part 2. Superiority of the one-point calibration method", Biosensors and Bioelectronics, 17:647-654 (2002).

Guardian® REAL-Time, Continuous Glucose Monitoring System, User Guide, Medtronic MiniMed, Inc., 184 pages (2006).

Kerner, et al., "The function of a hydrogen peroxide-detecting electroenzymatic glucose electrode is markedly impaired in human sub-cutaneous tissue and plasma", Biosensors & Bioelectronics, 8:473-482 (1993).

Koschinsky, et al., "Sensors for glucose monitoring: technical and clinical aspects", Diabetes/Metabolism Research and Reviews, 17:113-123 (2001).

Koschwanez, et al., "In vitro, in vivo and post explantation testing of glucose-detecting biosensors: Current methods and recommendations", Biomaterials, 28:3687-3703 (2007).

Pickup, et al., "In vivo glucose sensing for diabetes management: progress towards non-invasive monitoring", BMJ, 319, pp. 1-4 (1999).

Pickup, et al., "Responses and calibration of amperometric glucose sensors implanted in the subcutaneous tissue of man", Acta Diabetol, 30:143-148 (1993).

Wilson, et al., "Biosensors for real-time in vivo measurements", Biosensors and Bioelectronics, 20:2388-2403 (2005).

Wisniewski, et al., "Analyte flux through chronically implanted subcutaneous polyamide membranes differs in humans and rats", Am J Physiol Endocrinol Metab, 282:E1316-E1323 (2002).

PCT Application No. PCT/2018/039330, International Search Report and Written Opinion of the International Searching Authority mailed Sep. 17, 2018.

"Abbott Receives CE Mark for Freestyle® Libre, A Revolutionary Glucose Monitoring System for People with Diabetes," 8 pages (2023).

(56) References Cited

OTHER PUBLICATIONS

"DexCom (DXCM) Q1 2018 Results—Earnings Call Transcript" retrieved from https://seekingalpha.com/article/4168949-dexcom-dxcm-q1-2018-results-earnings-call-transcript on May 2, 2018, 4 pages.

"FDA authorizes first fully interoperable continuous glucose monitoring system, streamlines review pathway for similar devices," FDA News Release, retrieved from https://www.fda.gov/news-events/press-announcements/fda-authorizes-first-fully-interoperable-continuous-glucose-monitoring-system-streamlines-review on Mar. 27, 2018, 3 pages.

About Dexcom—Continuous Glucose Monitoring Company, 12 pages (2021).

Alva, S., et al., Accuracy of a 14-Day Factory-Calibrated Continuous Glucose Monitoring System With Advanced Algorithm in Pediatric and Adult Population With Diabetes, Journal of Diabetes Science and Technology, vol. 16(I), pp. 70-77 (2022).

ATTD Program, 4 pages (2009).

Cambridge Dictionary of American English, 3 pages (2000)—Recess.

Campbell, F. M., et al., Outcomes of using flash glucose monitoring technology by children and young people with type 1 diabetes in a single arm study, Pediatric Diabetes, pp. 1294-1301 (2018).

Deshmukh, H., et al., Effect of Flash Glucose Monitoring on Glycemic Control, Hypoglycemia, Diabetes-Related Distress, and Resource Utilization in the Association of British Clinical Diabetologists (ABCD) Nationwide Audit, Diabetes Care, 8 pages (2020).

Dexcom (DXCM) Company Profile, 2017 /Q4 Earnings call transcript, 12 pages (2017).

Dexcom G6 Continuous Glucose Monitoring System User Guide, 7 pages (2020).

Dexcomg6, Continuous Glucose Monitoring System, User Guide, 22 pages (2020).

DexcomG6, Start Here, Set up, Dexcom G6 Continuous Glucose Monitoring (CGM) System (G6), 8 pages (2019).

DexcomG6, Using Your G6, 7 pages (2020).

Drawing Sheets for U.S. Pat. No. 10,973,443 issued Apr. 13, 2021, 2 pages.

Email communication from Sophie Hood, Jan. 24, 2023, 6 pages.

Excerpts from Expert Report of Catharine M. Lawton—Ex. 36, Spruce Point Capital Management, Does Dexcom Really Have A Future If It Can't Match Abbott's Scale? 2 pages, Mar. 21, 2019.

Excerpts from U.S. Pat. No. 10,827,954, issued on Nov. 10, 2020, 7 pages.

Excerpts from U.S. Pat. No. 10,973,443, issued on Apr. 13, 2021, 22 pages.

General report of the German Diabetes Society on the state of diabetic patients and treatment methods for the year 2021, 15 pages (with English summary).

Haak, T., et al., Use of Flash Glucose-Sensing Technology for 12 months as a Replacement for Blood Glucose Monitoring in Insulin-treated Type 2 Diabetes, Diabetes Ther, 14 pages (2017).

Hall, Interview with Kevin Sayer, President and CEO of Dexcom About The New Dexcom G6, College Diabetes Network, 6 pages (2021).

Hoss et al., "Continuous glucose monitoring in the tissue: Do we really need to calibrate in-vivo?," Diabetes Technology & Therapeutics, vol. 11, No. 2, 23 pages (2009).

Hoss, et al., "Continuous Glucose Monitoring in Subcutaneous Tissue Using Factory-Calibrated Sensors: A Pilot Study", Diabetes Technology & Therapeutics, 12(8):591-597 (2010).

Hoss, et al., "Feasibility of Factory Calibration for Subcutaneous Glucose Sensors in Subjects With Diabetes", Journal of Diabetes Science and Technology, 8(1):89-94 (2014).

IEEE 100 The Authoritative Dictionary of IEEE Standards Terms, 7th Ed., 3 pages (2020).

Interview with Dexcom CEO, Dexcom CEO Kevin Sayer Explains G6, Written By: Michelle Boise, 9 pages (2018).

Joint Declaration of Funderburk, et al. for U.S. Appl. No. 15/963,828, 11 pages (2020).

Letter from Department of Health & Human Services, Food and Drug Administration, to Andy Balo, DexCom, Inc. re. P050012/S001, STS-7 Continuous Glucose Monitoring System dated May 31, 2007, 95 pages.

Letter from the Department of Health & Human Services, Food and Drug Administration to Abbott Diabetes Care, Inc. dated Mar. 12, 2008, regarding the Premarket Approval Application (PMA) for the FreeStyle Navigator Continuous Glucose Monitoring System, 7 pages.

Merriam-Webster's Collegiate Dictionary, 10th Ed., 4 pages (1999)—Housing and recess.

Merriam-Webster's Collegiate Dictionary, 10th Ed., 4 pages (1999)—Release and retain.

Microchip, microID® 13.56 MHz RFID System Design Guide, Microchip Technology Inc., 214 pages (2004).

Non-Final Office Action for U.S. Appl. No. 14/884,622 dated Jun. 13, 2018, 7 pages.

Non-Final Office Action for U.S. Appl. No. 17/030,030 dated Dec. 17, 2020, 7 pages.

Notice of Allowance for U.S. Appl. No. 15/963,828 dated Mar. 3, 2021, 32 pages.

Omnipod image, Exhibit 182, 2 pages, Sep. 22, 2022.

Response to Non-Final Office Action for U.S. Appl. No. 15/963,828 filed on Dec. 8, 2020, 17 pages.

Response to Restriction Requirement for U.S. Appl. No. 14/884,622 filed on Apr. 5, 2018, 15 pages.

Roussel, R., et al., Important Drop in Rate of Acute Diabetes Complications in People With Type 1 or Type 2 Diabetes After Initiation of Flash Glucose Monitoring in France: The RELIEF Study, 5 pages, American Diabetes Association, Diabetes Care (2021).

S&P Global Market Intelligence "DexCom, Inc. NasdaqGS:DXCM, Company Conference Presentation," 17 pages (2021).

S&P Global Market Intelligence "DexCom, Inc. NasdaqGS:DXCM, Company Conference Presentation," 10 pages (2020).

S&P Global Market Intelligence "DexCom, Inc. NasdaqGS:DXCM, Company Conference Presentation," 11 pages (2019).

Sayer, CGMS Changing Diabetes Management: Kevin Sayer, DIC Interview Transcript, Featuring Steve Freed, 11 pages (2019).

Sonix, Dexcom CEO—Prime Position in Our Market—Mad Money—CNBC.mp4, 4 pages (2023).

STS®—Seven Continuous Glucose Monitoring System User's Guide, 74 pages (2007).

Summary of Safety and Effectiveness Data, STS®—7 Continuous Glucose Monitoring System, DexCom, Inc., Date of Approval: May 31, 2007, 14 pages.

Tegnestedt, et al., "Levels and sources of sound in the intensive care unit—an observational study of three room types", Acta Anaesthesiologica Scandinavica, pp. 1-10 (2013).

The Chambers Dictionary, 4 pages (1998)—Retract.

The MiniMed Paradigm® REAL-Time Insulin Pump and Continuous Glucose Monitoring System, Insulin Pump User Guide, Paradigm® 522 and 722 Insulin Pumps, Medtronic MiniMed, Inc., 25 pages (2008).

The New Oxford American Dictionary, 3 pages (2001)—Retract.

The New Penguin English Dictionary, Penguin Books, 4 pages (2000)—Recess.

U.S. Food & Drug Administration, "Deciding When to Submit a 510(k) for a Change to an Existing Device, Guidance for Industry and Food and Drug Administration Staff," 78 pages (2017).

U.S. Food & Drug Administration, "Deciding When to Submit a 510(k) for a Software Change to an Existing Device, Guidance for Industry and Food and Drug Administration Staff," 32 pages (2017).

Watkin, "An Introduction to Flash Glucose Monitoring," 16 pages (2013).

Webster's New College Dictionary, 2 pages (2001)—Alcove.

Webster's Third New International Dictionary, 5 pages (1993)—Retract.

Armour et al., "Application of Chronic Intravascular Blood Glucose Sensor in Dogs," Diabetes, 39, 1519-1526 (1990).

Chen, "The Development and Application of Glucose Electrodes based on "Wired" Glucose Oxidase," the university of Texas at Austin, 168 pages, Dec. 2001.

(56)                    References Cited

OTHER PUBLICATIONS

Knobbe et al., Symposium Paper, "The Extended Kalman Filter for Continuous Glucose Monitoring," Diabetes Technology & Therapeutics, 7, 1, 15-27 (2005).
Schmidt, "Design and Development of a Wearable Glucose Sensor, In vitro and in vivo studies," Rijksuniversiteit Groningen (1963).
Dock, E. et al., "Multivariate data analysis of dynamic amperometric biosensor responses from binary analyte mixtures—applications of sensitivity correction algorithms", Talanta, 65, 2005 pp. 298-305.
FreeStyle Navigator Continuous Glucose Monitoring System, Dept of Health & Human Services, Food and Drug Administration, Mar. 12, 2008, 8 pages.
Hoss, U. et al., "Factory-Calibrated Continuous Glucose Sensors: The Science Behind the Technology", Diabetes Technology & Therapeutics, 2017, vol. 19, Suppl. 2, pp. S44-S50.
Choleau, C. et al., "Calibration of a subcutaneous amperometric glucose sensor Part 1. Effect of measurement uncertainties on the determination of sensor sensitivity and background current" Biosensors and Bioelectronices 17 (2002) 641-646.
Stephens Inc., Research Bulletin, "DexCom, Inc., A True Game Changer: The G6 Eliminates Fingersticks", (2018) 5 pages.
Dorland's Illustrated Medical 31$^{st}$ Edition Dictionary, definition of "fluid, intersitial", (2007), 3 pages.
Forlenza, G.P., et al., "Factory-Calibrated Continuous Glucose Monitoring: How and Why It Works, and the Dangers of Reuse Beyond Approved Duration of Wear", Diabetes Technology & Therapeutics, vol. 21, No. 4, (2019) 13 pages.
Frost, M.C., et al., "Implantable Chemical Sensors for real-time clinical monitoring progress and challenges" Current Opinion in Chemical Biology, (2002), 13 pages.
Koschinsky T., et al., "Sensors for glucose monitoring: technical and clinical aspects" Diabetes/Metabolism Research and Reviews, 17 (2001) 113-123.
Lodwig, V., et al., "Continuous Glucose Monitoring with Glucose Sensors: Calibration and Assessment Criteria", Diabetes Technology & Therapeutics, vol. 5, No. 4, (2003) pp. 573-587.
The American Hertiage® Medical Dictionary, definition of "catheter" and "interstitial fluid", (2007), 4 pages.
Vaddiraju, S., et al., "Technologies for Continuous Glucose Monitoring: Current Problems and Future Promises", Journal of Diabetes Science and Technology, vol. 4, Issue 6, (2010) 23 pages.
Ward, W.K., et al., Rise in background current over time in a subcutaneous glucose sensor in the rabbit: relevance to calibration and accuracy, Biosensors & Bioelectronics, 15, (2000) pp. 53-61.
Crawshaw, J., et al., "A Concise Course In A-Level Statistics—with Worked Examples", 2$^{nd}$ Edition, 1990, pp. 559-628.
Declaration of Thomas Foster of Taylor Wessing LLP, Hill House, 1 Little New St. London EC4A3TR ("Taylor Wessing"), signed on Jan. 30, 2024 (160 pages).
Description of the LINEST function in Excel 2003, https;//web.archive.org/web/20041119192208/http:/support.microsoft.com/kb/828533 2004, 16 pages.
File History for U.S. Pat. No. 10,709,364, Issued Jul. 14, 2020.
Fischer, U., "Fundamentals of Glucose Sensors", Diabetic Medicine, 1991; 8: 309-321.
Hanson, K. et al., "Comparison of Point Accuracy Between Two Widely Used Continuous Glucose Monitoring Systems", Journal of Diabetes Science and Technology, 2024, pp. 1-10.
Padgette et al., "Guide to Bluetooth Security, Recommendations of the National Institute of Standards and Technology," National Institute of Standards and Technology, U.S. Department of Commerce, Special Publication 800-121 Revision 1, 48 pages, May 2007.
PMA Final Decisions Rendered for May 2007, The Wayback Machine, U.S. Food and Drug Administration, 21 pages.
Premarket Approval (PMA) on Seven Plus Continuous Glucose Monitoring System, Notice date: Jun. 28, 2007, 3 pages.
Specification Bluetooth System Experience More, 134 pages, Jun. 2010.
Specification Bluetooth System Wireless connections, 92 pages, Nov. 2003.
TI-82 Graphing Calculator Guidebook, Texas Instruments, 1993, 278 pages.
Abbott Press Release—"Abbott Receives CE Mark for FreeStyle® Libre, A Revolutionary Glucose Monitoring System for People with Diabetes" retrieved from https://abbott.mediaroom.com/2014-09-03-Abbott-Receives-CE-Mark-for-FreeStyle-Libre-a-Revolutionary-Glucose-Monitoring-System-for-People-with-Diabetes/, Sep. 3, 2014, 3 pages.
Abbott Press Release—"Abbott Receives FDA Approval for the FreeStyle Libre Pro™ System, A Revolutionary Diabetes Sensing Technology for Healthcare Professionals to Use with their Patients" retrieved from https://abbott.mediaroom.com/2016-09-28-Abbott-Receives-FDA-Approval-for-the-FreeStyle-Libre-Pro-System-a-Revolutionary-Diabetes-Sensing-Technology-for-Healthcare-Professionals-to-use-with-their-Patients/, Sep. 28, 2016, 5 pages.
Abbott Press Release—"Abbott's FreeStyle® Libre 14 Day Flash Glucose Monitoring System Now Approved in U.S." retrieved from https://abbott.mediaroom.com/2018-07-27-Abbotts-FreeStyle-R-Libre-14-Day-Flash-Glucose-Monitoring-System-Now-Approved-in-U-S/, Jul. 27, 2018, 3 pages.
Anzhsn, National Horizon Scanning Unit Horizon Scanning Report, "GlucoWatch® G2 Biographer for the non-invasive monitoring of glucose levels", 46 pages, May 2004.
Baltensperger, "Vials, Caps, Septa & Various Products in Comparison", CTC Analytics AG, Switzerland, 3 pages, Apr. 9, 2020.
Beardsall, et al., "The continuous glucose monitoring sensor in neonatal intensive care", Arch Dis Child Fetal Neonatal, 90:F307-F310 (2005).
Black et al., Handbook of Biomaterial Properties, Springer Science+Business Media, Dordrecht, 5 pages (1998).
Cather, CGM Frustrations Survey dated Jun. 2020, 37 pages in *Abbott Diabetes Care Inc., et al. v. Dexcom, Inc.,* Case No. 1:21-cv-00977-KAJ (District of Delaware).
Choudhary, et al., Insulin Pump Therapy With Automated Insulin Suspension in Response to Hypoglycemia, Reduction in nocturnal hypoglycemia in those at greatest risk, Diabetes Care, vol. 34, pp. 2023-2025 (2011).
Clinical Trials, Competitor and Ecosystem Players dated Jun. 25, 2020, 29 pages in *Abbott Diabetes Care Inc., et al. v. Dexcom, Inc.,* Case No. 1:21-cv-00977-KAJ (District of Delaware).
Congress.gov, About the Congressional Record, Feb. 22, 2022, 3 pages.
Declaration of Dr. Anthony Edward Cass in Support of Petition for Inter Partes Review of U.S. Pat. No. 11,020,031 in *Abbott Diabetes Care Inc. v. Dexcom, Inc.,* Case No. IPR2024-00890, In the United States Patent and Trademark Office, Before the Patent Trial and Appeal Board, May 10, 2024, 138 pages.
Declaration of Dr. Anthony Edward Cass in Support of Petition for Inter Partes Review of U.S. Pat. No. 10,709,364 in *Abbott Diabetes Care Inc. v. Dexcom, Inc.,* Case No. IPR2024-00841, In the United States Patent and Trademark Office, Before the Patent Trial and Appeal Board, Apr. 26, 2024, 101 pages.
Declaration of Karl R. Leinsing, MSME, PE, in Support of Abbott's Motion for Summary Judgment dated May 19, 2023, 81 pages in *Abbott Diabetes Care Inc., et al. v. Dexcom, Inc.,* Case No. 1:21-cv-00977-KAJ (District of Delaware).
Declaration of Sylvia D. Hall-Ellis, Ph.D. in Inter Partes Review of U.S. Pat. No. 10,709,364 in *Abbott Diabetes Care Inc. v. Dexcom, Inc.,* Case No. IPR2024-00841, In the United States Patent and Trademark Office, Before the Patent Trial and Appeal Board, Apr. 25, 2024, 203 pages.
Declaration of Sylvia D. Hall-Ellis, Ph.D. in Inter Partes Review of U.S. Pat. No. 11,020,031 in *Abbott Diabetes Care Inc. v. Dexcom, Inc.,* Case No. IPR2024-00890, In the United States Patent and Trademark Office, Before the Patent Trial and Appeal Board, May 3, 2024, 232 pages.
Effectiveness and Safety Study of the DexCom™ G4 Continuous Glucose Monitoring System, DexCom, Inc., U.S. National Library of Medicine, ClinicalTrials.gov Identifier: NCT01111370, 4 pages (2017).

(56) References Cited

OTHER PUBLICATIONS

E-mail Communication from Christopher M. Dougherty regarding Bi Monthly Global Commercial Insights Meeting dated Dec. 17, 2019, 69 pages in *Abbott Diabetes Care Inc., et al. v. Dexcom, Inc.,* Case No. 1:21-cv-00977-KAJ (District of Delaware).

Encyclopedia of Polymer Science and Engineering, Second Edition, vol. 15, Scattering to Structural Foams, John Wiley & Sons, Inc., Parts 1-16, 132 pages (1989).

FDA Premarket Approval (PMA) for Seven Plus Continuous Glucose Monitoring System, Notice Date: Jun. 28, 2007, 3 pages.

Federal Register, vol. 76, No. 120, Jun. 22, 2011, pp. 36542-36543.

Design U.S. Appl. No. 29/101,218, filed Feb. 25, 1999, 11 pages.

Fraser, Chapter 1, "An Introduction to in vivo Biosensing: Progress and Problems", Biosensors in the Body: Continuous in vivo Monitoring, 30 pages (1997).

FreeStyle Libre 2 HCP Pulse, Mar. 2021 Report, dated Mar. 1, 2021, 14 pages in *Abbott Diabetes Care Inc., et al. v. Dexcom, Inc.,* Case No. 1:21-cv-00977-KAJ (District of Delaware).

Godek, et al., Chapter 2, "The Macrophage in Wound Healing Surrounding Implanted Devices", In Vivo Glucose Sensing, 36 pages (2010).

Gross, et al., "Performance Evaluation of the MiniMed® Continuous Glucose Monitoring System During Patient Home Use", Diabetes Technology & Therapeutics, vol. 2, No. 1, pp. 49-56 (2000).

Hager, "Why Double Electrocoat and Powder Coat?", MerCruiser, 5 pages (1999).

Hamilton Company, Selecting the Right Syringe, retrieved from https://web.archive.org/web/20030625132534/http:/www.hamiltoncompany.com/product/syringe/Syringe%20Selection.html, 4 pages (2003).

Henning, Chapter 5, "Commercially Available Continuous Glucose Monitoring Systems", In Vivo Glucose Sensing, 50 pages (2010).

Hon, Urging FDA to Act Promptly to Approve Artificial Pancreas Technologies, Congressional Record (Bound Edition), vol. 157 (2011), Part 13, 3 pages.

Kowalski, Can We Really Close the Loop and How Soon? Accelerating the Availability of an Artificial Pancreas: A Roadmap to Better Diabetes Outcomes, Diabetes Technology & Therapeutics, vol. 11, pp. S-113-S-119 (2009).

Lesperance, et al., "Calibration of the Continuous Glucose Monitoring System for Transient Glucose Monitoring", Diabetes Technology & Therapeutics, vol. 9, No. 2, pp. 183-190 (2007).

Letter from Department of Health & Human Services to Mr. Andy Balo, Dexcom, Inc. re. P050012/S001, STS-7 Continuous Glucose Monitoring System, dated May 31, 2007, 7 pages.

MD&DI, Silicone Rubber for Medical Device Applications, retrieved from https://www.mddionline.com/orthopedic/silicone-rubber-for-medical-device-applications, 8 pages (Nov. 1, 1999).

Petition for Inter Partes Review of U.S. Pat. No. 11,020,031 in *Abbott Diabetes Care Inc. v. Dexcom, Inc.,* Case No. IPR2024-00890, In the United States Patent and Trademark Office, Before the Patent Trial and Appeal Board, May 10, 2024, 86 pages.

Pickup, et al., Semi-Closed-Loop Insulin Delivery Systems: Early Experience with Low-Glucose Insulin Suspend Pumps, Diabetes Technology & Therapeutics, vol. 13, No. 7, pp. 695-698 (2011).

Project Status Update, Glucose Sensor Applicator Dexcom (project #2554), Design Concepts, Inc., 6 pages (2014).

Scheduling Order dated Sep. 19, 2023, 14 pages in *Abbott Diabetes Care Inc., et al. v. Dexcom, Inc.,* Case No. 1:23-cv-00239-KAJ (District of Delaware).

Schlosser, et al., Chapter 5, "Biocompatibility of Active Implantable Devices", Biosensors in the Body: Continuous in vivo Monitoring, 34 pages (1997).

Seagrove Partners, International Diabetes Device, 2022 Blue Book dated 2022, 143 pages in *Abbott Diabetes Care Inc., et al. v. Dexcom, Inc.,* Case No. 1:21-cv-00977-KAJ (District of Delaware).

STS-7 Continuous Glucose Monitoring System—P050012/S001, Approved May 31, 2007, FDA U.S. Food and Drug Administration, 1 page.

The Wayback Machine—The Apple Rubber Seal Design Guide, Apple Rubber Products, Inc., Parts 1-8, 182 pages (2003).

Wampler, et al., Chapter 6, "Carbon Black", Rubber Compounding, Chemistry and Applications, pp. 239-284 (2004).

Wikipedia, The Free Encyclopedia, "Gender of connectors and fasteners", retrieved from https://en.wikipedia.org/w/index.php?title= Gender of connectors and fasteners& oldid= 1225173660, 6 pages (May 22, 2024).

Wilson et al., Chapter 1, "Introduction to the Glucose Sensing Problem," In Vivo Glucose Sensing, 32 pages (2010).

Wisniewski, et al., "Characterization of implantable biosensor membrane biofouling", Fresenius J Anal Chem, 366:611-621 (2000).

Z-Carbon Connector Data Sheet, retrieved from http://www.zaxisconnector.com/SS_zc.shtml, Z-Axis Connector Company, 2 pages (2004).

Z-Silver Connector Data Sheet, retrieved from http://www.zaxisconnector.com/SS_zs.shtml, Z-Axis Connector Company, 2 pages (2004).

Libre LinkUp User Guide, 1999, 28 pgs.

Extract from the privacy notice for LibreView, 2024, 7 pgs.

Mosa et al., "A Systematic Review of Healthcare Applications for Smartphones," BMC Medical Informatics and Decision Making, 12:67 (2012) 32 pgs.

Custodio et al., "A Review on Architectures and Communications Technologies for Wearable Health-Monitoring Systems," Sensors 12:13907-13946 (2012).

CNEDIMTS, Dexcom G6, Feb. 25, 2020, 28 pgs.

Order 8, Jun. 2023 modifying the conditions of registration of the Freestyle Libre 2, 3 pgs.

UPC Court of Appeal, Feb. 26, 2024, 335/2023, 38 pgs.

Annex E3 Excerpts from the "German Health Report Diabetes 2023" of the German Diabetes Society, Nov. 14, 2022, 12 pgs.

\* cited by examiner

Associate sensor with lot-specific uncertainty value.
400

Associate sensor with pre-determined sensor model specific lag.
410

Associate sensor with lot-specific membrane lag.
420

Group lot-specific measurement uncertainty into operating glucose ranges.
430

Store values as pre-determined fixed values associated with a specific sensor model.
440

ARTIFICIAL PANCREAS INTEGRATED CGM ARCHITECTURES AND DESIGNS

RELATED APPLICATION

The present application claims priority to U.S. patent application Ser. No. 16/017,584, filed Jun. 25, 2018, which claims priority under 35 U.S.C. § 119(e) to U.S. Provisional Application No. 62/525,164 filed Jun. 26, 2017, entitled "Artificial Pancreas Integrated CGM Architectures and Designs," the disclosure of which is incorporated herein by reference for all purposes.

BACKGROUND

The present invention relates to continuous glucose monitoring (CGM) systems or flash glucose monitoring with insulin therapy. More specifically, the present invention relates to a continuous glucose monitoring system including computing devices to utilize detected analyte levels and stored sensor information for monitoring, diagnosis and analysis.

The technical advancements and commercial adoption of smartphones and cloud-based computing has facilitated the development of glucose monitoring systems and methods, for example by promoting standardized communication technologies such as Bluetooth® and the World-Wide-Web.

SUMMARY

An environment for realizing artificial pancreas systems that utilize communication technologies and other technologies is described. Systems, devices, and methods for integrating continuous glucose monitoring (CGM) or flash glucose monitoring with insulin therapy are provided. One or more embodiments of the present invention include a system for managing a patient's glucose level including an analyte sensor to generate and store data signals for measurements of the patient's glucose level made by the analyte sensor; an insulin pump; and sensor electronics operatively coupled to the analyte sensor. The sensor electronics comprise a memory storing one or more predetermined characteristics associated with the sensor electronics. The system further includes a computing device in electronic communication with the sensor electronics, the computing device comprising a processor configured to operate the sensor electronics to (i) receive the generated data signals, (ii) obtain the one or more predetermined sensor characteristics from the memory and (iii) execute a closed-loop algorithm to provide insulin delivery instructions to an insulin pump by at least using the data signals and predetermined characteristics.

In an embodiment, a method includes a first step involving measuring/determining sensor characteristics during the manufacturing process of the sensor. The second step involves storing these sensor characteristics into the sensor system. The third step involves a mechanism to retrieve and use these characteristics in a system that executes a closed-loop algorithm or executes a sensor signal processing algorithm (e.g. for a glucose monitoring device).

In certain example embodiments, an artificial pancreas includes an insulin delivery system (e.g.: an insulin pump, Bluetooth® enabled smart insulin pen, Bluetooth® low energy enabled smart insulin pen), a glucose sensor, and a closed-loop algorithm which generates insulin delivery commands to the pump based, in part, on inputs from the glucose sensor. The artificial pancreas includes hardware and software which work in conjunction with other analytes as well, and are not limited to glucose.

In embodiments the system further includes mechanisms needed for the components to communicate. The technical advancements and commercial adoption of smartphones and cloud-based computing has facilitated the development of artificial pancreas-type systems and methods, for example, by promoting standardized communication technologies such as Bluetooth® and the world-wide-web. An environment for realizing artificial pancreas systems that utilize these and other technologies is described below. While devices described herein are described with respect to glucose as an example of an analyte, in implementations the hardware and software described below may be used in conjunction with other analytes.

DETAILED DESCRIPTION

Architecture Considerations

Figure 1:
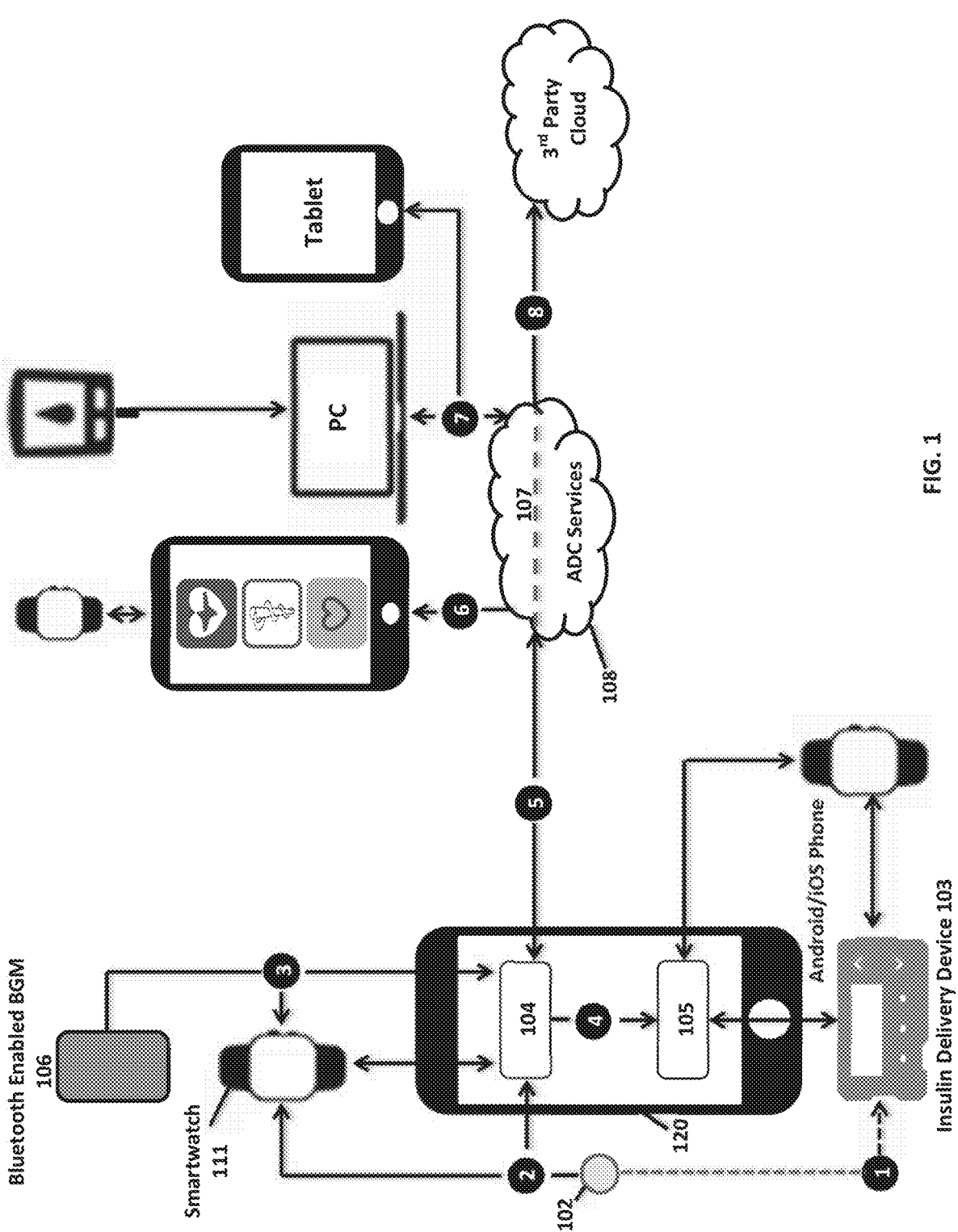
FIG. 1 illustrates a glucose monitoring system in accordance with an embodiment.

FIG. 1 illustrates a glucose monitoring system in accordance with an embodiment. Under the embodiment of FIG. 1, a glucose sensor is in communication with an intermediary device (e.g., smartphone operating a software application) which operates to control an insulin delivery device (e.g., insulin delivery device, such as an insulin pump 103).

In the embodiment of FIG. 1, sensor device 102 includes a processor and a memory storing executable instructions for a glucose calculation algorithm. Pump 103 includes a processor and memory storing executable instructions for a closed-loop insulin delivery algorithm.

In the illustration of FIG. 1, the embodiment's glucose sensor control device (SCD) 102 includes components including a housing, a sensor for in vivo placement that extends from the housing, processor and other electronics for controlling the sensor and collecting glucose measurement results, a power supply, and communication circuitry for communicating with other devices. SCD 102 can communicate directly with the insulin pump 103 over numerous kinds of communication networks. For example, in the illustration of FIG. 1, SCD 102 is in communication with insulin pump 103 via Bluetooth®. As used herein, the term "Bluetooth®" includes all varieties of Bluetooth® including standard (classic) Bluetooth® or Bluetooth® Low Energy (also called Bluetooth® SMART, Bluetooth® SMART READY, BTLE, BLE) communication (1); in this embodiment of FIG. 1, the glucose calculation algorithm is located on the sensor device 102 and the closed-loop glucose level, insulin delivery algorithm is located at the pump 103. SCD 102 also communicates via Bluetooth® to other intermediate devices (2), such as a reader device 120 (shown here to be a smartphone but could also be a dedicated use device) or a smartwatch 111, to provide user display of glucose data and to allow user input into and control of the sensor/system.

In an embodiment as in FIG. 1, the intermediate devices may also communicate via Bluetooth® to the insulin pump 103, for display of glucose data and to allow user input into and control of the system. Other devices can communicate to the intermediate devices via Bluetooth® such as a Bluetooth® enabled self-monitoring blood glucose meter (SMBG meter) 106 that can provide redundant glucose measurements for use in the closed-loop system. Finally, the intermediate devices can also communicate over the Internet (5) with a cloud-based server 108 to provide data archiving, report generation and data backup.

As mentioned, SCD 102 may communicate with a number of intermediate devices, either in an alternative fashion or simultaneously in addition. The number and types of intermediate devices may depend on, among other aspects, how much power each of these devices demands based on any constraints placed upon the underlying Bluetooth® protocol. SCD 102, which may have the tightest power constraint in the system, can provision its available battery power in order to meet the demands of multiple wireless connections with the least impact to those devices with which it communicates.

In implementations, SCD 102 accomplishes this provisioning by, among other possibilities, making concessions on one or more Bluetooth® parameters, such as communication interval, advertising interval, or transmission power. SCD 102 may also adjust its measurement cycle to achieve optimal system performance. For example, if SCD 102 were to be connected to a pump in addition to a phone, it could increase the connection interval to the phone to make up for the additional communication events needed for the pump. SCD 102 could follow a default algorithm for this kind of provisioning, with adjustment options made available to an intermediate device, such as smartphone.

Among other advantages, Bluetooth® has become a commercial standard and has incorporated low energy features that make it suitable for use with a low power consumption sensor device. However, in implementations other suitable communication technologies can be utilized instead of or in addition to Bluetooth®.

In embodiments, a physical communication connection interface can be included with the SCD 102. For example, a wired USB interface may be provided with SCD 102 for communication between SCD 102 and the insulin pump 103, to ensure communication reliability.

In an alternative embodiment, the closed-loop algorithm is stored on an intermediate device. For instance, the closed-loop algorithm may be stored in a memory of the smartphone 120 or the smartwatch 111. In such an embodiment, the SCD 102 communicates directly with the intermediate device, which in turn provides insulin delivery commands to the pump 103. An advantage of this embodiment is the potential modular approach where any closed-loop algorithm smartphone App 104 could be easily integrated with a Bluetooth® enabled sensor device and a Bluetooth® enabled insulin pump. For example, smartwatch 111 is likely worn continuously, and an embodiment where the closed-loop algorithm is located in the smartwatch 111 may thus provide advantages.

In embodiments, app 104 can exchange data with authorized 3rd party apps 105 running on the same smartphone device 120 through an app-to-app data exchange (e.g., using native operating system (OS) frameworks like, e.g., Health-Kit).

In another embodiment the closed-loop algorithm is stored in the cloud 108. SCD 102 communicates the glucose data to one or more computing devices which are part of cloud 108 via the intermediate device, and the computing devices communicate the resulting insulin command to the pump via the intermediate device (e.g., 120, 111). Alternatively or in addition, SCD 102 and insulin pump 103 communicate directly via the internet to the cloud 108. One or more computing devices, SCD 102 and/or insulin pump 103 include features to compensate for internet latency and ensure reliability.

In embodiments, the communication between an SCD 102 and an on-body insulin pump 103 may occasionally be interrupted. In recognition, in an embodiment of the system, multiple communication paths are provided for data from SCD 102 to reach the insulin pump 103. For instance, the system may have multiple communication paths, e.g., a communication path to transmit glucose data directly from SCD 102 to the pump 103, and another path from SCD 102 to the pump 103 via a smartphone 120, and yet another path via a smartwatch 111. The closed-loop algorithm on the pump 103 would accept data from any of these multiple paths and could also check the data from each path to confirm that they are consistent. These redundant communication paths could also communicate other inputs intended for the closed-loop algorithm. Alternatively, the closed-loop algorithm could be redundantly stored on each of the smartphone 120, smartwatch 111, SCD 102, etc., so that the closed-loop insulin delivery instructions could be redundantly and independently transmitted to the insulin pump 103.

Another alterative embodiment is for SCD 102 to also act as a hub for other inputs to the system. Among other advantages, SCD 102 and the pump 103 may be attached to the patient's body, whereas the intermediate devices may not always be located with the body or have relatively less reliable communication interfaces for a real-time system such as an artificial pancreas. In an embodiment where SCD 102 acts as a hub, SCD 102 is the central storage for device configuration and other important information such as alarm parameters, such as alarm thresholds, snooze, and turn-off. For instance, if one connected device snoozes an alarm, it would communicate this to SCD 102, which would in turn communicate this to the other connected devices. The connected devices would locally store and keep these parameters up to date.

Connection of the system to computing devices via a cloud also provides a means for monitoring the system for safety. For instance, a medical service may be provided that monitors the closed-loop insulin delivery commands for values that exceed some threshold (either immediate values or cumulative) and notifies personnel to contact the patient to ensure that everything is Ok.

In another embodiment, the closed-loop algorithm includes a different interface module for different types of SCDs 102. This module provides the interface between the closed-loop algorithm and a particular SCD 102. This module provides for reliable communication regardless of any difference in the communication protocol between types of SCDs 102. Furthermore, because different kinds of SCD 102 have different performance characteristics, the module could be used to "normalize" the glucose data provided by SCD 102 so that the data output from the module as an input to the closed-loop control algorithm has comparable performance compared to the output from modules for different SCDs 102.

One embodiment of this normalization module is to provide an ergodic measure of the sensor system's noise model. For example, sensor "system 1" may have a random uncertainty of ±5 mg/dL in the low end and ±10% at the high end, while sensor "system 2" may have a smaller lower end uncertainty but larger high end uncertainty. Incorporating this information can be implemented by adding an upper and lower confidence interval based on these aggregate ergodic measures. The values can be obtained from clinical study data of the appropriate sensor systems.

In yet another embodiment of this normalization module, the aggregate lag between the sensor output time series and a preferred reference glucose time series (e.g. venous blood glucose, arterial blood glucose, or capillary blood glucose) obtained from clinical study data can be used by the closed-loop algorithm. For example, closed-loop algorithms that are based on output feedback, such as the PID or the e-PID, can use this information by calculating an upper and lower sensor glucose bound for every sensor output values. Closed-loop algorithms that are model-based, such as the MPC, can incorporate the amount of lag explicitly into their state observer when calculating the optimal insulin delivery profile or any countering agent such as glucagon.

The net effect of the two embodiments described above, is a normalization module that allows the closed-loop algorithm to throttle the aggressiveness of the insulin delivery (or any countering agent). A sensor system with a relatively smaller noise or smaller lag allows for the same controller to respond more aggressively than a sensor with a relatively larger noise or larger lag as described in the two embodiments above.

Power Consumption Considerations

Embodiments recognize advantages for minimizing the power consumption of SCD 102 to be low; these advantages include minimizing the size and cost of the device. As such, in implementations methods are used for keeping the power consumption of devices in the system low, such as for connected devices to only request data when they need it.

For instance, a closed-loop controller may only request data at a low sample rate when glucose levels are stable (and receive a burst of data that includes multiple samples), but request at a higher sample rate when glucose levels are changing. The sensor device may provision system resources based on demand from connected devices.

Security Considerations

Since the artificial pancreas system controls delivery of the potentially dangerous drug (insulin), access to the system should be carefully controlled. Standard means of securing access to intermediate devices may be used such as passwords and biometric access features.

However, to prevent unauthorized access to the SCD 102 communications, an alternate communication mechanism may be designed into SCD 102 that allows pairing via Bluetooth®. An example of an alternate mechanism for commercially available Bluetooth® enabled devices is an actuatable button.

Furthermore, to reduce cost and improve reliability associated with buttons, an alternate pairing solution is to use NFC as an "out of band" communication to exchange secrets for pairing and bonding. For example, many smartphones include NFC reader capability. In implementations, NFC enabled reader 120 communicates with an NFC tag in a sensor packaging, which shares a common secret code with the SCD 102. For pairing, reader 120 is placed near the NFC tag in the packaging, and pairing then occurs automatically without requiring further user interaction.

Alternatively, in implementations where a computing device (e.g., smartphones) has a camera, a barcode on the packaging could be read using the camera, which would produce a similar effect as under NFC. These communication methods function at very close proximity and are not easily intercepted by a third party, thus improving security.

Embodiments recognize that data encryption provided by the current Bluetooth® designs can be compromised and that tools are available to decrypt the Bluetooth® data packets encrypted with standard Bluetooth® encryption methods. Consequently, a more secure approach may be implemented by using application level encryption to encrypt the data so that the data security is not compromised even if the Bluetooth® level encryption is broken, such as by using Elliptic Curve cryptography and Diffie-Hellman key exchange in the application designs on top of the Bluetooth® encryption.

Another mechanism for improving the security of the pairing with SCD 102 is for the device-to-be-paired, such as a smartphone 120 or insulin pump 103, to require the user to input a code as part of the pairing process, via the user interface. The code, such as the sensor serial number or portion of the serial number, may be preinstalled in the sensor device memory (e.g., during manufacturing). The code would also be provided to the user in the sensor device packaging, user guide, or on SCD 102 itself. As part of the "out-of-box" pairing process the user would enter this code, then the device-to-be-paired would transmit the entered code to the sensor device, and the sensor device would compare this code with the code stored in its memory. If the code matches, then SCD 102 would proceed with the pairing; if the code does not match an appropriate error message will be sent to the device-to-be-paired and the pairing process will be suspended.

After initial pairing, the device-to-be-paired can download to SCD 102 another code that is attributed to the user; this code is stored on the sensor device. The code may be specified by the user, such as a PIN (personal identification number) or code by randomly generated by the device-to-be-paired. Referring to this code as a PIN, the PIN can now be used for other devices to pair with the sensor device. When another device-to-be-paired attempts to pair with the sensor device, it sends this PIN. The sensor device compares this PIN with the PIN stored in its memory. If the code matches, then the sensor device would proceed with the pairing; if the code does not match an appropriate error message will be sent to the device-to-be-paired and the pairing process will be suspended.

Algorithm Considerations

The closed-loop algorithm primarily utilizes glucose measurement data as an input;

additionally, other measurements or inputs may be utilized. Examples of such inputs include past insulin delivered, current insulin command, meal information, activity information, glucose sensor temperature, blood pressure measurement, etc. Some of these measurements may be made with sensors collocated or integrated with SCD 102 and communicated directly from SCD 102 to the algorithm.

Other measurements may be transmitted or input into the smartphone device, integrated and provided and/or transmitted to the algorithm. For instance, SCD 102 may also include a temperature sensor and an accelerometer, and readings from these sensors can be integrated with the glucose data in a communication transmission and transmitted to the algorithm. These readings can be used to predict physiological responses to treatment. Specifically, a sudden drop in sensor temperature may indicate an impending hyperglycemic event.

In addition, glucose data from multiple sources may be used in the closed-loop algorithm. For instance, the sensor device may provide the primary source of glucose data for the algorithm. However, with the connectivity provided by smartphone devices, other sources of glucose data, for instance from a Bluetooth® enabled SMBG meter, can be utilized in the algorithm. The multiple sources of glucose data can be utilized in the closed-loop control algorithm using standard control design techniques. It could also be used to estimate sensor data uncertainty, which can also be used in the control algorithm.

The glucose calculation algorithm that converts raw glucose sensor measurements to glucose values may be located on SCD 102, on an intermediate communication device, such as a smartphone 120 or a cloud server 108, or at the insulin pump 103. The output of this algorithm provides the glucose values that are used in the closed-loop algorithm. Alternatively, the system may provide glucose measurements directly into the closed-loop algorithm. The glucose sensor device (or intermediate communication device) may provide both raw glucose measurements and calculated glucose measurements in the communication transmission intended for closed-loop control. Alternatively, SCD 102 (or intermediate communication device) may provide alternatively calculated glucose results; for instance, one result utilizing lag correction in the calculation algorithm and another without lag correction.

If insulin delivery information from the pump and/or closed-loop algorithm as well as other relevant information such as meal (e.g. start of a meal, relative amount, amount of carbohydrates, amount of fat or protein, consumption of alcohol) can be made available to SCD 102, then the sensor glucose calculation can take these information into account to reconcile between actual glucose change and/or change in direction versus an artifact to be rejected/ignored/compensated for. Information regarding insulin delivery can be based on available insulin delivery information, such as recent bolus amount (i.e. how many units) and profile (e.g. square wave, normal, or extended), a detected occlusion that prevents or slows insulin delivery, or latest basal insulin infusion rate.

In some closed-loop systems, in addition to the latest insulin delivery rate command, every update may include temporary basal rate to be used should there be any interruption in the insulin pump's command in the near future. In this case, the temporary basal can also be used by the sensor glucose algorithm to obtain a better estimate of the latest glucose value as well as near future glucose values.

Some sensor systems, may utilize a hybrid closed-loop algorithm in conjunction with, or in place of, a closed-loop algorithm. For example, additional input may be provided to control the insulin pump in conjunction with the algorithm. In embodiments, sensor systems may switch between modes where the closed-loop algorithm is used, and where a hybrid closed-loop algorithm is used. In embodiments, the hybrid closed-loop algorithm may be used for calculation of insulin delivery profiles as described herein.

In embodiments, a patient's initial conditions may be used as a basis for use of a closed-loop or hybrid closed-loop algorithm. For example, a patient may be characterized via open-loop glucose dynamics, and these characterizations used as initial conditions for a closed-loop or hybrid closed-loop algorithm.

The estimate of the near future glucose values as described, in combination with recent past glucose measurement values, can also be used to provide a time estimate for other components of the system such as a connected smartwatch, pump controller, or smartphone. This time estimate may include a pre-determined or adjustable glucose level threshold. For example, let the glucose level threshold be set at 5 mg/dL (or it can be a hybrid threshold of 5 mg/dL at low glucose, and 20% at high glucose). Then, at any given time, the sensor glucose algorithm may include a time estimate in the sensor signal payload.

This time estimate corresponds to the estimated duration in the near future when sensor glucose may have changed by at least that threshold. As a result, non-critical components may be able to query or update its values at a longer time interval in order to conserve its own power.

In certain applications, such as pilot closed-loop system studies, this time estimate can also be incorporated into the hazard mitigation of the study in order to alert a remote monitoring service or the study participant when the time estimate is shorter than a pre-determined value.

Continuing with the scenario of insulin delivery information from the pump and/or closed-loop algorithm as well as other relevant information such as meal being made available to the sensor, then a time-of-day pattern comparison similar to the Ambulatory Glucose Profile (AGP), normalized by the known insulin delivery and meal information, can be done to determine whether the glucose measurement values in the past few hours are out of the range of the known variation of the same time of day from the last few days. One use of this information is to remind the patient that there may be something different about this day, such as missed meal bolus, missed a meal, change in stress levels causing additional hyperglycemia, sensor adhesive failure, or an infusion set failure.

Another input into the closed-loop algorithm is various measures of uncertainty in the glucose measurement or in the anticipated glucose measurements. Uncertainty can be used in the closed-loop algorithm to adjust how much weight the algorithm places on certain algorithm inputs vs. glycemic state determined from the model incorporated into the closed-loop control system. One measure of glucose measurement uncertainty is to utilize uncertainty estimates for the glucose readings and rate-of-change generated from the glucose calculation algorithm.

In certain embodiments, sensor systems include pre-determined specifications or requirements on uncertainty. The pre-determined specification or requirements in certain embodiments are sensor system-specific. For example, a particular sensor system type has a pre-determined specification on uncertainty having a standard deviation of 11 mg/dL across the entire operating range of the sensor. Another sensor system type may have a pre-determined uncertainty defined based on coefficient of variation, for example a 14% coefficient of variation. A third sensor system can have a pre-determined uncertainty based on standard deviation characteristics, for example, a 20 mg/dL standard deviation for readings up to 154 mg/dL, and a variance of 13% for readings above 154 mg/dL. When the closed-loop algorithm obtains a reading from the sensor system, the pre-determined uncertainty associated with the particular sensor system in certain embodiments is either implicitly or explicitly used to process sensor signals.

For example, in certain embodiments, the closed-loop algorithm may take the pre-determined uncertainty into account implicitly by adopting a pre-determined rule that reduces the aggressiveness of the closed-loop controller when the latest sensor reading is associated with a higher uncertainty. By doing so, the algorithm may cause the closed-loop controller to behave more aggressively (e.g., with regard to insulin delivery) when the latest sensor reading is associated with a lower uncertainty.

In other embodiments, the closed-loop algorithm may take the pre-determined uncertainty into account explicitly by directly linking, or otherwise providing, the uncertainty information provided by and specific to the particular sensor system to a state observer component of the closed-loop controller. For example, in a state feedback-based approach that employs a state observer, such as a Kalman Filter, the influence of the latest sensor reading is tempered by the assumed uncertainty from that sensor reading. Without this sensor system type specific uncertainty information, a state observer such as a Kalman Filter in a state feedback-based approach may need to determine the measurement uncertainty separately. This may involve making a prospective determination that does not change once the determination is completed.

In certain embodiments, the pre-determined specification of uncertainty may be the expected error of each sensor system type as a function of elapsed time since the sensor start. In embodiments, due to sensor response drift, a sensor system can have a pre-determined uncertainty, e.g. a −3%/day average drift with a 5%/day standard deviation across a population of sensors of that type. Another sensor system can have a −0.5%/day average drift with a 20%/day standard deviation. The closed-loop algorithm can either use this information implicitly or explicitly. In the absence of such information, the closed-loop system may make a prospective assumption on this sensor characteristic.

In certain embodiments, the specification of uncertainty may be described by parameters associated with a particular sensor type. These parameters may take various forms when plotted, such as lines or curves. In embodiments, the parameters may correspond to an expected mean value from a priori sensor population data, a median, a mode, or other calculations which may be used to describe the population aggregate response over time. Upper and lower bounds can be determined from interquartile range or other methods.

A central trend and bounds can be pre-determined and carried by the sensor system type in various ways. In an embodiment, the sensor system carries information regarding the equations governing how the values change over time, and the necessary parameters for them. One example is the use of an exponential system of the form NormalizedResponse(t)=a1*[exp(-a2 t)−exp(-a3 t)] to describe the change of values over time. For such a system, the knowledge of the equation, plus the values for a1, a2, and a3, are then specific for that sensor system In one embodiment, an extension is made on the ergodic noise example previously described. In this particular case, the sensor glucose algorithm may link its artifact and/or noise rejection sub module to generate a time varying uncertainty value. For example, when this sub module detects a higher than average temporary increase in noise or dropouts (aka Pressure Induced Sensor Attenuation), then the closed-loop algorithm can adjust its controller aggressiveness accordingly.

In addition, if the sensor glucose algorithm alters the effective bandwidth of its filter, an estimate of the overall sensor system lag is also updated. For example, suppose a sensor system is determined to have an aggregate lag of 6 minutes relative to its preferred reference glucose as determined from clinical study data. When the sensor glucose system is operating nominally, a value of 6 minutes is made available in the sensor glucose payload for the closed-loop algorithm to use. When the sensor glucose system detects a condition that warrants more smoothing, or when other conditions trigger the sensor glucose system to apply more smoothing, then the value is increased accordingly.

Uncertainty can also be estimated from other inputs to the system. For instance, increased sensor temperature fluctuations could be detected as in indication that the glucose measurement may be more uncertain. Also, other inputs to the system such as a meal start indicator may be used as a means to indicate greater glucose measurement uncertainty, in particular with glucose measurements that exhibit lag.

In another aspect of the algorithm, when higher uncertainty is detected, the system can respond in ways to reduce the uncertainty. For instance, in response to high uncertainty, the system can request a faster sampling rate from SCD 102. SCD 102 could provide a faster sampling rate at times of uncertainty as part of an overall power management algorithm that makes other concessions to make up for the additional power to provide more data. For example, such an algorithm could sample at slower than nominal rates at other times of stable glucose. Alternatively, the sensor algorithm can detect high uncertainty, and provide data to the closed-loop control algorithm at a faster rate. If data at a faster rate is not available because of power budget limitations, the user could be notified of the situation and even be allowed to override the limitation if desired.

In other aspects of the algorithm, when a low insulin rate is detected, the glucose calculation algorithm may use more lax data quality checks when validating glucose values for further use. Alternatively, when high rates of insulin infusion are detected, the data quality checks may become strict. For example, if the user's glucose value is fluctuating in a wide range over a period of time and the user is doing frequent insulin adjustments, algorithm calculation can switch to a different configuration to require more data points in the future to accurately calculate the current real-time glucose value. Also, if a lapse in communication with the glucose sensor occurs, when the communication is reestablished, the control algorithm may request the missing data from SCD 102, or alternatively, SCD 102 may provide the missing data. The control algorithm can use this missing data to update the model state that is used in the algorithm. Depending on the closed-loop algorithm, the duration and sample interval of the recovered sensor glucose may vary. The sensor glucose system may provide a minimum number of points required to properly recreate the continuous sensor signal in that specified duration, or it may provide data in the sample interval and duration specified by the requesting closed-loop system.

In embodiments as in FIG. 1, informatics 107 may be included to provide real-time or near real-time access to selected data, through an API, to authorized apps 105 and/or devices (e.g., MySugr, Fitbit, or caregiver reader apps). The informatics 107 enable patients, health care providers (HCPs), and caregivers to upload data from supported devices (e.g., BGM 106, reader devices 120 (dedicated, smartphone, etc.) and to produce reports and view them on demand. Furthermore informatics 107 can provide access to selected data to authorized 3rd party cloud-based services (e.g., data brokers like Validic, or EMR systems like Practice Fusion).

In another aspect of the algorithm, existing closed-loop algorithms attempt to control glucose to a fixed glucose value or a fixed range of values. This disclosure contemplates using a predetermined "normal" prandial glucose profile as a closed-loop target instead of a fixed target. For example, the typical post-prandial glucose excursion could be allowed by the algorithm, causing the correction from the algorithm to be attenuated during this time. This may avoid closed loop overshoot.

In one embodiment of this "normal" profile, the sensor glucose system provides an upper target and a lower target time series points to cover the entire 24 hours (in the sense of the AGP). The system may start with a predetermined upper and lower target time series generated by the HCP or the closed-loop study organizer. As sensor glucose data is collected, a historic profile is created, containing historic lower time series. This historic lower time series reflects recent past hypoglycemia risk. If the historic lower time series is much lower than the lower target time series, the upper target time series may need to be adjusted upwards around that time of day. This prevents the closed-loop system from attempting to follow an unreasonable upper goal, by overexerting its efforts in the most difficult periods at the expense of increased risk of hypoglycemia. Over time, as other areas (of time of day) are improved, as the closed-loop system adaptive parameters improve, and as the patient makes better use of meal announcements and other use adjustments, the historic lower time series may no longer be far below the lower target time series in most areas of time of day. This allows the upper target time series to be adjusted down. The net result increases the chance of attaining better glucose control in the long run without subjecting the patient to unnecessarily high risk of hypoglycemia.

Another aspect of the closed-loop algorithm is to perform a system status check based on comparing the predicted glucose response based on planned interventions such as insulin delivery or meal inputs, with the actual measured glucose, to detect that the intervention did not occur or was different than planned. One example is detecting occlusion in the insulin delivery apparatus when the measured glucose is less than the predicted glucose. This detection could be used in conjunction with a pump-centric occlusion detection, as a redundant check.

Figure 2:
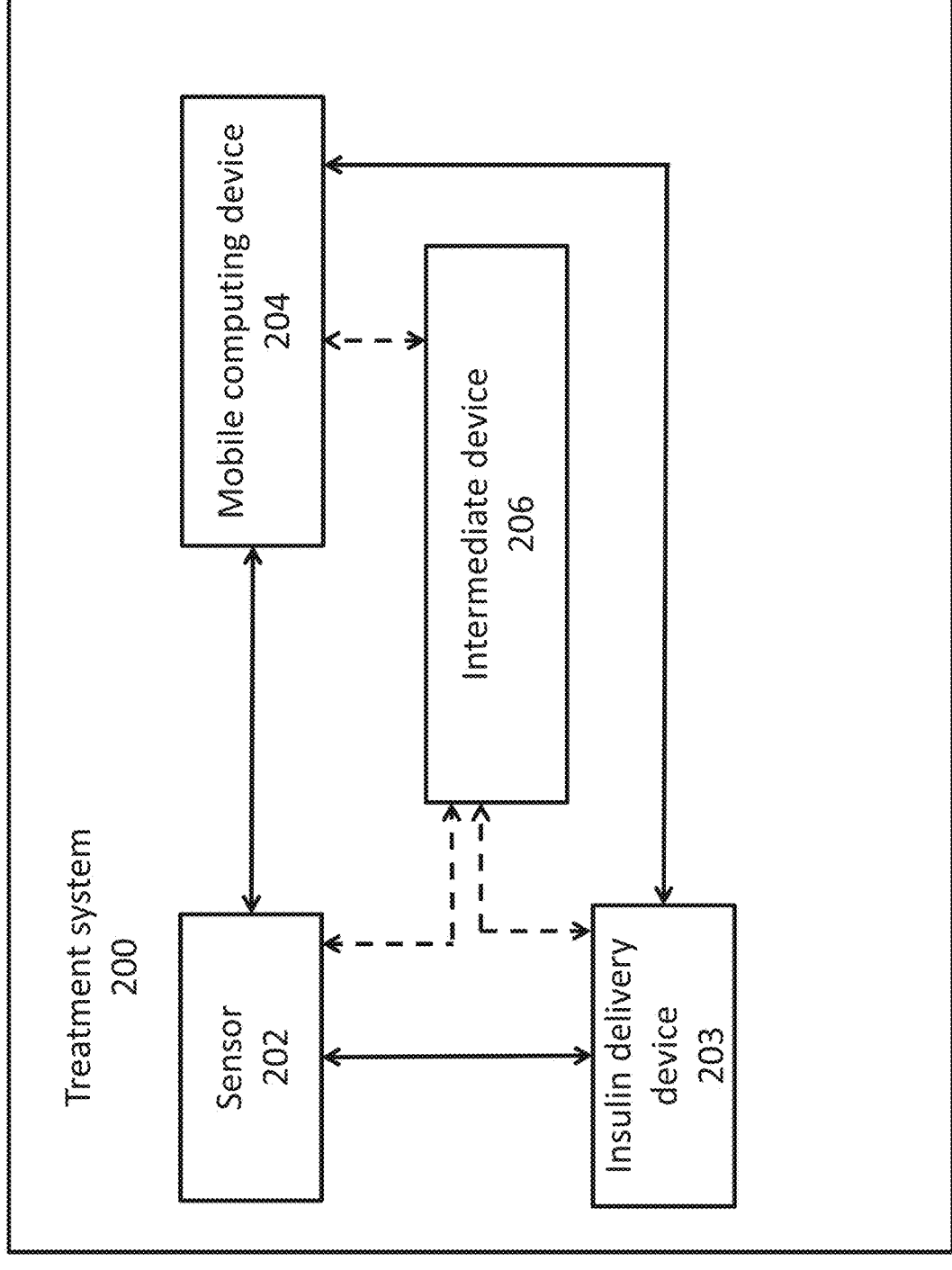
FIG. 2 illustrates a diabetes treatment system according to an embodiment.

FIG. 2 illustrates a diabetes treatment system according to an embodiment. Treatment system 200 includes a sensor 202, which includes electronics for measuring an analyte level, storing data (e.g., measurement data, sensor-related data), and transmitting and receiving data (e.g., via Bluetooth® communication). Sensor 202 is in communication with insulin delivery device 203 and a mobile computing device 204. Mobile computing device 204 includes a processor and memory to receive measurement data and/or other data from sensor 202, perform calculations, and transmit instructions to insulin delivery device 203. In embodiments, mobile computing device 204 can be a smartphone operating a software application configured to perform the previously mentioned operations. Furthermore, in the embodiment of FIG. 2, intermediate device 206 operates as an intermediary with respect to the one or more functions of mobile computing device 204 (e.g., communication, analyte calculations, error correction). In implementations, intermediate device 206 may include a processor and programming to perform one or more other operations which could otherwise be performed on mobile computing device 204 (e.g., calculations; instructions). While a single intermediate device is shown in the illustration of FIG. 2, in embodiments multiple intermediate devices may be used.

Figure 3:
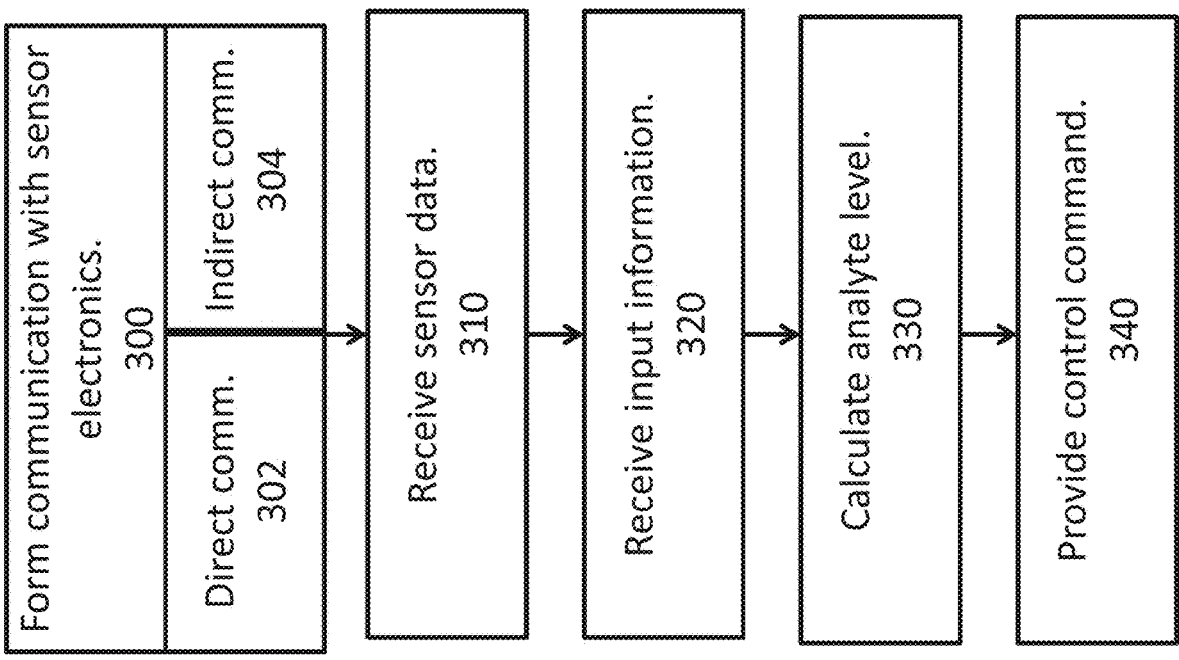
FIG. 3 illustrates a method for using a glucose monitoring system in an embodiment.

FIG. 3 illustrates a method for using a glucose monitoring system in an embodiment. A method as described in FIG. 3 may, in embodiments, be implemented with the systems described in FIGS. 1 and 2. Reference is made in describing FIG. 3 to the elements of systems of FIGS. 1 and 2.

At (300) a communication is formed with sensor electronics, either directly (302) or indirectly (304). In an embodiment, a closed-loop algorithm module (e.g., a computing device operating the closed-loop algorithm module) communicates with an on-body component of a sensor system (e.g., via a Bluetooth® Low Energy communication connection). Sensor data is received or otherwise obtained (310). For example, the device operating the closed-loop algorithm module may receive analyte level measurements from a sensor. Input information is received (320). For example, the device operating the closed-loop algorithm module may receive uncertainty data from the on-body component's memory. The data from (310) and (320) may be received from different devices; for example, the analyte level information and the input information may be received from different transmitting devices. An analyte level is calculated based, at least in part, on the received sensor data and uncertainty data (330), and a control command is provided based on the analyte level (340). For example the control command may control the amount of insulin delivered by an insulin delivery device.

In an embodiment, a closed-loop algorithm module is in direct communication with the on-body component of a sensor system (e.g. via BTLE). The measurement uncertainty information can be used to determine the aggressiveness level of the control command (e.g. how much insulin to dose at any given time). If sensor lag information is available, the closed-loop algorithm can also take that knowledge in addition to the measurement uncertainty in order to adjust the dosing decision accordingly. An example is when the closed-loop algorithm employs a form of state observer (e.g. a Kalman Filter, a Linear Quadratic Gaussian controller, or a model predictive controller), where the lag and measurement uncertainty information become parameters that are explicitly needed by the state observer calculations. Without this mechanism, every time a new sensor or sensor lot or sensor system is used, the controller parameters may need to be tuned accordingly.

In a further embodiment, a sensor signal processing algorithm is the final user of the information. Information from the on-body component can be used by the sensor signal processing algorithm to maximize the algorithm's performance. For example, when a sensor whose measurement uncertainty is relatively low is connected to the sensor signal processing algorithm module, the algorithm can adjust to perform less smoothing and increase the extent of lag correction closer to the maximum allowable setting. When the membrane lag or overall system lag is relatively small, the sensor signal processing algorithm module can decrease the extent of lag correction closer to the minimum allowable setting.

In the case of an indirect communication between a closed-loop algorithm module and the on-body component of a sensor system via a Reader, information from the on-body component can be further modified by the sensor signal processing algorithm module in the Reader. For example, the sensor signal processing algorithm can modulate the sensor information such as the measurement uncertainty in terms of a time varying variability or a time varying bias that reflects a priori in-vivo information. The sensor signal processing algorithm can also run wear-time fault detection and compensation, or any available comparison against reference BG. The Reader then communicates the information to the closed-loop algorithm module. As a result, the same closed-loop algorithm as described in the first embodiment can use the same type of information, but with the benefit of additional temporal refinement / adjustment by the sensor signal processing algorithm module in the Reader.

Figure 4:
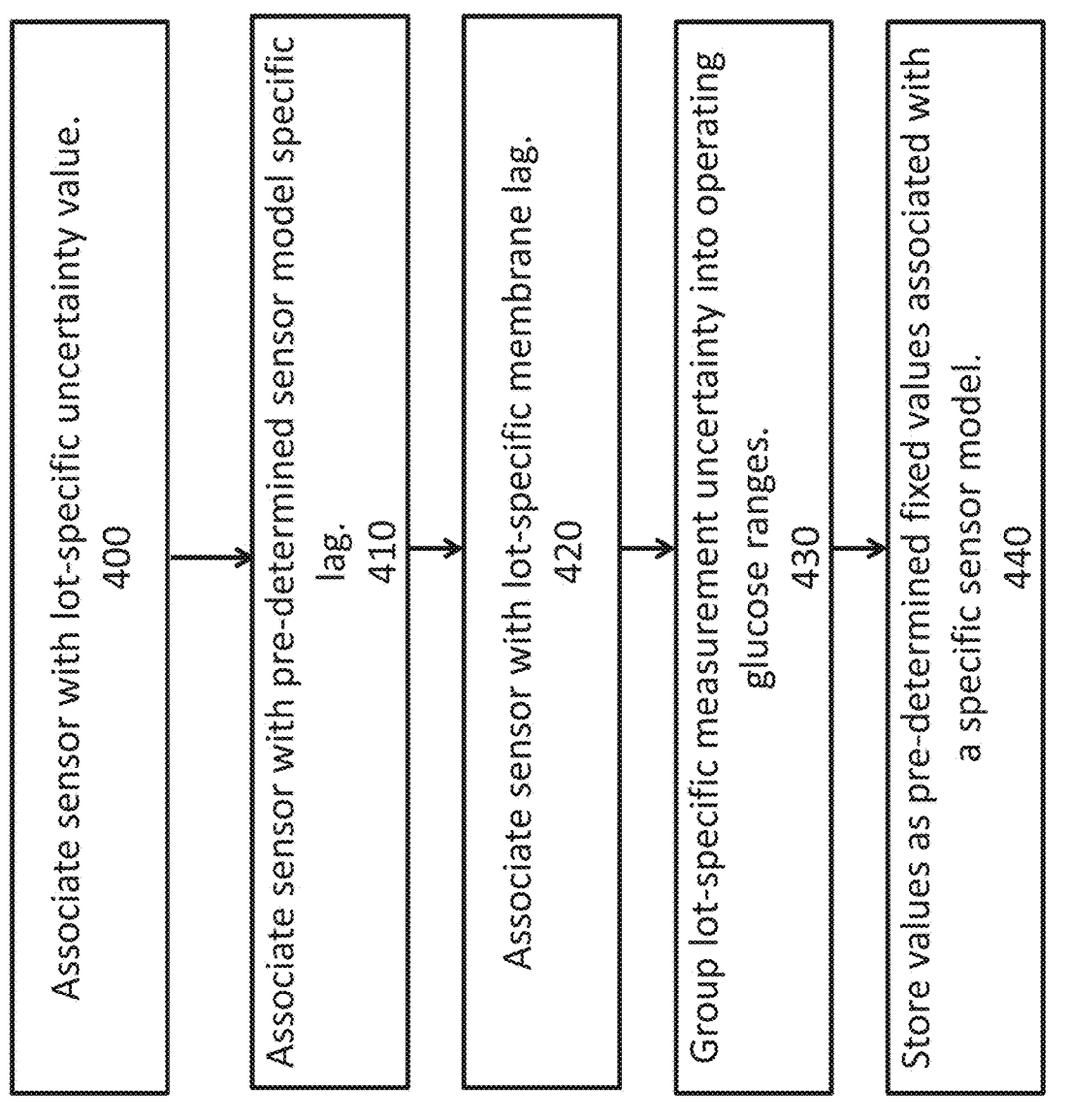
FIG. 4 illustrates a method for preparing a sensor assembly for use in a glucose monitoring system in an embodiment.

FIG. 4 illustrates a method for preparing a sensor assembly for use in a glucose monitoring system in an embodiment. A method as described in FIG. 4 may, in embodiments, be implemented with the systems described in FIGS. 1 and 2. Reference is made in describing FIG. 4 to the elements of systems of FIGS. 1 and 2.

During the manufacturing process, a sensor lot is characterized by performing a series of tests on a sample batch. One of the information obtained from this batch sample is the sensor-to-sensor in-vitro uncertainty (e.g. in terms of coefficient of variation). In addition, the response time of each sample is measured, relative to stepwise changing concentration of glucose in the testing system. Numerous kinds of information and pre-determined characteristics (e.g., lot-specific measurement uncertainty value, pre-determined sensor model specific lag, lot-specific membrane lag) can be captured during the manufacturing process.

A sensor in a sensor lot is associated with a lot-specific measurement uncertainty value (400). In embodiments, this can be obtained by measuring the coefficient of variation (CV) of the in-vitro batch sample's signal response to glucose at various known glucose concentrations relative to the curve fitted to the data. It can also be obtained in terms of the standard deviation of the same dataset, inter-quartile range of the same dataset, or other statistical measures that reflect the measurement uncertainty.

The sensor is associated with a pre-determined sensor model specific lag (410). The sensor model specific lag can be influenced by the intended sensor insertion site and the type of reference BG used to assess system performance. For example, a transcutaneous sensor that measures interstitial glucose relative to a capillary BG reference can be assumed to have a relatively larger lag than the same transcutaneous sensor that measures the same interstitial glucose relative to a reference interstitial fluid concentration.

The sensor is associated with a lot-specific membrane lag (420). A lot-specific membrane lag can be calculated from the time response of the batch sample sensors relative to the stepwise changing known glucose concentration in the testing system.

In embodiments, the lot-specific measurement uncertainty may be grouped into several operating glucose ranges (430). For example, the use of 3 glucose ranges will then store 3 different lot-specific measurement uncertainty for the low, medium, and high glucose ranges, where the boundaries of each glucose ranges are pre-determined.

The values are stored as pre-determined fixed values associated with a specific sensor model (440). For example the measurement uncertainty and sensor lag data may be stored in a memory of the sensor.

All features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. Express recitation of every possible combination and substitution is overly burdensome, especially given that the permissibility of each and every such combination and substitution will be readily recognized by those of ordinary skill in the art upon reading this description.

All software described herein, and all actions of devices can be performed or executed with processing circuitry, such as, e.g., a microprocessor, a microcontroller, an applications processor, a communications processor, a programmable gate array, or one or more of the preceding examples operating in conjunction with each other. Non-transitory memories can store a plurality of instructions that, when executed by the processing circuitry, cause the software to be performed and/or the described actions to be taken. Examples of non-transitory memory include volatile and nonvolatile memory, RAM, ROM, hard disk drives, and the like.

What is claimed is:

1. A system for managing a patient's glucose levels, the system comprising:
    a glucose sensor configured to generate data signals corresponding to the patient's glucose levels;
    an insulin pump;
    sensor electronics comprising a memory storing a predetermined glucose measurement uncertainty, and a processor operatively coupled to the glucose sensor and configured to determine glucose levels based on the generated data signals and a lag correction, and to output the glucose levels and the predetermined glucose measurement uncertainty; and
    a computing device in communication with the sensor electronics, the computing device comprising a processor configured to (i) receive the outputted glucose levels from the sensor electronics, (ii) receive the predetermined glucose measurement uncertainty in the outputted glucose levels, (iii) execute a closed-loop algorithm, including adjusting an amount of weight placed on the outputted glucose levels using the predetermined glucose measurement uncertainty, and (iv) provide insulin delivery instructions to the insulin pump using an output from the closed-loop algorithm.

2. The system of claim 1, wherein the lag correction is determined during lot manufacturing of the sensor electronics.

3. The system of claim 1, wherein the lag correction corresponds to one or more sensor characteristics determined during lot manufacturing from a sample of glucose sensors in the lot.

4. The system of claim 1, where the computing device communicates with the sensor electronics over a Bluetooth® communication link.

5. The system of claim 1, wherein the lag correction includes at least one of a lot-specific membrane lag and a sensor model-specific lag.

6. The system of claim 1, wherein the computing device communicates with the sensor electronics over the Internet.

7. The system of claim 1, wherein the processor is further configured to receive additional glucose data from a glucose data source in addition to the glucose sensor, and to execute the closed-loop algorithm to provide insulin delivery instructions to the insulin pump by further using the additional glucose data.

8. The system of claim 7, wherein the processor is further configured to receive the additional glucose data over multiple communication paths, and to confirm that the additional data is consistent with the glucose levels determined by the glucose sensor.

9. The system of claim 1, wherein the computing device comprises at least one of (i) a smartphone, (ii) a smartwatch, or (iii) a cloud-based server.

10. The system of claim 1, wherein the predetermined glucose measurement uncertainty is based on a standard deviation across an operating range of the glucose sensor.

11. The system of claim 1, wherein the predetermined glucose measurement uncertainty is based on a coefficient of variation.

12. The system of claim 1, wherein the predetermined glucose measurement uncertainty is an expected error of the glucose sensor as a function of elapsed time since a start of the glucose sensor.

13. The system of claim 1, wherein the lag correction is an aggregate lag relative to a reference glucose value.

14. The system of claim 1, wherein the predetermined glucose measurement uncertainty is used to adjust at least one of an aggressiveness of insulin delivery or signal smoothing of the data signals corresponding to the patient's glucose levels.

15. A system for managing a patient's glucose level, the system comprising:

a glucose sensor configured to generate data signals corresponding to the patient's glucose levels, sensor electronics comprising a memory storing a predetermined glucose measurement uncertainty, and a processor operatively coupled to the glucose sensor and configured to determine glucose levels based on the generated data signals and a lag correction, and to output the glucose levels and the predetermined glucose measurement uncertainty; and a computing device in communication with the sensor electronics, the computing device comprising a processor configured to (i) receive the outputted glucose levels from the sensor electronics, (ii) receive the predetermined glucose measurement uncertainty in the outputted glucose levels, (iii) execute a closed-loop algorithm, including adjusting an aggressiveness of insulin delivery based on the predetermined glucose measurement uncertainty, and (iv) provide insulin delivery instructions to an insulin pump using an output from the closed-loop algorithm.

16. The system of claim 15, wherein adjusting the aggressiveness of insulin delivery comprises reducing the aggressiveness when a most recent glucose level of the outputted glucose levels is associated with a higher uncertainty than an uncertainty associated with a preceding glucose level of the outputted glucose levels.

17. The system of claim 15, wherein adjusting the aggressiveness of insulin delivery comprises increasing the aggressiveness when a most recent glucose level of the outputted glucose levels is associated with a lower uncertainty than an uncertainty associated with a preceding glucose level of the outputted glucose levels.

18. The system of claim 1, wherein the processor of the computing device is further configured to receive a glucose measurement determined by a blood glucose meter.

* * * * *